(12) United States Patent
Weber

(10) Patent No.: US 8,052,745 B2
(45) Date of Patent: Nov. 8, 2011

(54) ENDOPROSTHESIS

(75) Inventor: Jan Weber, Maastricht (NL)

(73) Assignee: Boston Scientific SciMed, Inc., Maple Grove, MN (US)

( * ) Notice: Subject to any disclaimer, the term of this patent is extended or adjusted under 35 U.S.C. 154(b) by 27 days.

(21) Appl. No.: 11/854,966

(22) Filed: Sep. 13, 2007

(65) Prior Publication Data

US 2009/0076588 A1 Mar. 19, 2009

(51) Int. Cl.
*A61F 2/06* (2006.01)
(52) U.S. Cl. ............... 623/1.42; 623/1.15; 623/1.38
(58) Field of Classification Search ............... 623/1.42, 623/1.43–1.46
See application file for complete search history.

(56) References Cited

U.S. PATENT DOCUMENTS

| | | |
|---|---|---|
| 2,950,187 A | 8/1960 | Ototani |
| 3,560,362 A | 2/1971 | Kasamatsu et al. |
| 3,569,660 A | 3/1971 | Houldcroft |
| 3,687,135 A | 8/1972 | Stroganov et al. |
| 3,758,396 A | 9/1973 | Vieth et al. |
| 3,868,578 A | 2/1975 | Oldham |
| 3,910,819 A | 10/1975 | Rembaum et al. |
| 3,948,254 A | 4/1976 | Zaffaroni |
| 3,952,334 A | 4/1976 | Bokros et al. |
| 3,993,072 A | 11/1976 | Zaffaroni |
| 4,002,877 A | 1/1977 | Banas |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,334,327 A | 6/1982 | Lyman et al. |
| 4,401,546 A | 8/1983 | Nakamura et al. |
| 4,532,929 A | 8/1985 | Mattei et al. |
| 4,539,061 A | 9/1985 | Sagiv |
| 4,542,539 A | 9/1985 | Rowe et al. |
| 4,585,652 A | 4/1986 | Miller et al. |
| 4,634,502 A | 1/1987 | Callahan et al. |
| 4,655,771 A | 4/1987 | Wallsten |
| 4,657,544 A | 4/1987 | Pinchuk |
| 4,665,896 A | 5/1987 | LaForge et al. |
| 4,705,502 A | 11/1987 | Patel |
| 4,713,070 A | 12/1987 | Mano |
| 4,725,273 A | 2/1988 | Kira |
| 4,733,665 A | 3/1988 | Palmaz |
| 4,767,418 A | 8/1988 | Deininger et al. |
| 4,784,659 A | 11/1988 | Fleckenstein et al. |
| 4,800,882 A | 1/1989 | Gianturco |

(Continued)

FOREIGN PATENT DOCUMENTS

AU 739 507 11/1998

(Continued)

OTHER PUBLICATIONS

Deepwater. "Galvanic Series". Galvanic Series. Downloaded from <http://corrosion-doctors.org/Definitions/galvanic-series.htm> on Mar. 11, 2011.*

(Continued)

*Primary Examiner* — Thomas J Sweet
*Assistant Examiner* — Andrew Iwamaye
(74) *Attorney, Agent, or Firm* — Fish & Richardson P.C.

(57) ABSTRACT

In embodiments a stent includes a stent body and a wire-form carrying a drug located along the stent body.

20 Claims, 4 Drawing Sheets

U.S. PATENT DOCUMENTS

| | | |
|---|---|---|
| 4,804,382 A | 2/1989 | Turina et al. |
| 4,886,062 A | 12/1989 | Wiktor |
| 4,954,126 A | 9/1990 | Wallsten |
| 4,976,692 A | 12/1990 | Atad |
| 4,994,071 A | 2/1991 | MacGregor |
| 5,024,671 A | 6/1991 | Tu et al. |
| 5,059,211 A | 10/1991 | Stack et al. |
| 5,061,275 A | 10/1991 | Wallsten et al. |
| 5,061,914 A | 10/1991 | Busch et al. |
| 5,073,365 A | 12/1991 | Katz et al. |
| 5,079,203 A | 1/1992 | Pinnavaia |
| 5,091,024 A | 2/1992 | DeBold et al. |
| 5,091,205 A | 2/1992 | Fan |
| 5,102,403 A | 4/1992 | Alt |
| 5,120,322 A | 6/1992 | Davis et al. |
| 5,125,971 A | 6/1992 | Nonami et al. |
| 5,147,370 A | 9/1992 | McNamara et al. |
| 5,163,958 A | 11/1992 | Pinchuk |
| 5,195,969 A | 3/1993 | Wang et al. |
| 5,205,921 A | 4/1993 | Shirkanzadeh |
| 5,234,457 A | 8/1993 | Andersen |
| 5,236,413 A | 8/1993 | Feiring |
| 5,236,447 A | 8/1993 | Kubo et al. |
| 5,270,086 A | 12/1993 | Hamlin |
| 5,279,292 A | 1/1994 | Baumann et al. |
| 5,290,585 A | 3/1994 | Elton |
| 5,292,558 A | 3/1994 | Heller et al. |
| 5,302,414 A | 4/1994 | Alkhimov et al. |
| 5,304,121 A | 4/1994 | Sahatjian |
| 5,304,195 A | 4/1994 | Twyford, Jr. et al. |
| 5,306,286 A | 4/1994 | Stack et al. |
| 5,314,453 A | 5/1994 | Jeutter |
| 5,322,520 A | 6/1994 | Milder |
| 5,342,348 A * | 8/1994 | Kaplan ............ 604/891.1 |
| 5,348,553 A | 9/1994 | Whitney |
| 5,356,433 A | 10/1994 | Rowland et al. |
| 5,360,440 A | 11/1994 | Andersen |
| 5,366,504 A | 11/1994 | Andersen et al. |
| 5,380,298 A | 1/1995 | Zabetakis et al. |
| 5,383,935 A | 1/1995 | Shirkhanzadeh |
| 5,385,776 A | 1/1995 | Maxfield et al. |
| 5,397,307 A | 3/1995 | Goodin |
| 5,405,367 A | 4/1995 | Schulman et al. |
| 5,421,955 A | 6/1995 | Lau et al. |
| 5,439,446 A | 8/1995 | Barry |
| 5,443,458 A | 8/1995 | Eury |
| 5,443,496 A | 8/1995 | Schwartz et al. |
| 5,443,500 A | 8/1995 | Sigwart |
| 5,449,373 A | 9/1995 | Pinchasik et al. |
| 5,449,382 A | 9/1995 | Dayton |
| 5,458,627 A | 10/1995 | Baranowski, Jr. et al. |
| 5,462,575 A | 10/1995 | Del Corso |
| 5,464,450 A | 11/1995 | Buscemi et al. |
| 5,464,650 A | 11/1995 | Berg et al. |
| 5,468,574 A | 11/1995 | Ehrenberg et al. |
| 5,474,797 A | 12/1995 | Sioshansi et al. |
| 5,500,013 A | 3/1996 | Buscemi et al. |
| 5,514,154 A | 5/1996 | Lau et al. |
| 5,527,337 A | 6/1996 | Stack et al. |
| 5,536,573 A | 7/1996 | Rubner et al. |
| 5,545,208 A | 8/1996 | Wolff et al. |
| 5,549,664 A | 8/1996 | Hirata et al. |
| 5,551,954 A | 9/1996 | Buscemi et al. |
| 5,578,075 A | 11/1996 | Dayton |
| 5,587,200 A | 12/1996 | Lorenz et al. |
| 5,587,507 A | 12/1996 | Kohn et al. |
| 5,591,222 A | 1/1997 | Susawa et al. |
| 5,591,224 A | 1/1997 | Schwartz et al. |
| 5,599,352 A | 2/1997 | Dinh et al. |
| 5,603,556 A | 2/1997 | Klink |
| 5,605,696 A | 2/1997 | Eury et al. |
| 5,607,463 A | 3/1997 | Schwartz et al. |
| 5,609,629 A | 3/1997 | Fearnot et al. |
| 5,614,549 A | 3/1997 | Greenwald et al. |
| 5,624,411 A | 4/1997 | Tuch |
| 5,628,787 A | 5/1997 | Mayer |
| 5,629,077 A | 5/1997 | Turnlund et al. |
| 5,632,771 A | 5/1997 | Boatman et al. |
| 5,632,840 A | 5/1997 | Campbell |
| 5,649,951 A | 7/1997 | Davidson |
| 5,658,327 A | 8/1997 | Altman et al. |
| 5,672,242 A | 9/1997 | Jen |
| 5,674,192 A | 10/1997 | Sahatjian et al. |
| 5,674,242 A | 10/1997 | Phan et al. |
| 5,676,685 A | 10/1997 | Razavi |
| 5,679,440 A | 10/1997 | Kubota |
| 5,690,670 A | 11/1997 | Davidson |
| 5,693,085 A | 12/1997 | Buirge et al. |
| 5,693,928 A | 12/1997 | Egitto et al. |
| 5,697,967 A | 12/1997 | Dinh et al. |
| 5,700,286 A | 12/1997 | Tartaglia et al. |
| 5,716,981 A | 2/1998 | Hunter et al. |
| 5,721,049 A | 2/1998 | Marcolongo et al. |
| 5,725,570 A | 3/1998 | Heath |
| 5,733,925 A | 3/1998 | Kunz et al. |
| 5,741,331 A | 4/1998 | Pinchuk |
| 5,744,515 A | 4/1998 | Clapper |
| 5,749,809 A | 5/1998 | Lin |
| 5,749,880 A | 5/1998 | Banas et al. |
| 5,758,562 A | 6/1998 | Thompson |
| 5,759,192 A | 6/1998 | Saunders |
| 5,761,775 A | 6/1998 | Legome et al. |
| 5,769,883 A | 6/1998 | Buscemi et al. |
| 5,769,884 A | 6/1998 | Solovay |
| 5,773,925 A | 6/1998 | Kimura et al. |
| 5,776,184 A | 7/1998 | Tuch |
| 5,779,904 A | 7/1998 | Ruderman et al. |
| 5,780,807 A | 7/1998 | Saunders |
| 5,788,626 A | 8/1998 | Thompson |
| 5,788,687 A | 8/1998 | Batich et al. |
| 5,788,979 A | 8/1998 | Alt et al. |
| 5,797,898 A | 8/1998 | Santini, Jr. et al. |
| 5,800,511 A | 9/1998 | Mayer |
| 5,815,904 A | 10/1998 | Clubb et al. |
| 5,817,046 A | 10/1998 | Glickman |
| 5,824,045 A | 10/1998 | Alt |
| 5,824,048 A | 10/1998 | Tuch |
| 5,824,077 A | 10/1998 | Mayer |
| 5,830,217 A | 11/1998 | Ryan |
| 5,833,715 A | 11/1998 | Vachon et al. |
| 5,837,007 A | 11/1998 | Altman et al. |
| 5,837,275 A | 11/1998 | Burrell et al. |
| 5,840,387 A | 11/1998 | Berlowitz-Tarrant et al. |
| 5,843,089 A | 12/1998 | Sahatjian et al. |
| 5,843,172 A | 12/1998 | Yan |
| 5,852,277 A | 12/1998 | Gustafson |
| 5,854,382 A | 12/1998 | Loomis |
| 5,858,556 A | 1/1999 | Eckert et al. |
| 5,869,140 A | 2/1999 | Blohowiak et al. |
| 5,873,904 A | 2/1999 | Ragheb et al. |
| 5,876,756 A | 3/1999 | Takada et al. |
| 5,879,697 A | 3/1999 | Ding et al. |
| 5,880,661 A | 3/1999 | Davidson et al. |
| 5,882,335 A | 3/1999 | Leone et al. |
| 5,891,108 A | 4/1999 | Leone et al. |
| 5,891,191 A | 4/1999 | Stinson |
| 5,899,935 A | 5/1999 | Ding |
| 5,902,266 A | 5/1999 | Leone et al. |
| 5,906,759 A | 5/1999 | Richter |
| 5,907,893 A | 6/1999 | Zadno-Azizi et al. |
| 5,922,005 A | 7/1999 | Richter et al. |
| 5,922,021 A | 7/1999 | Jang |
| 5,928,247 A | 7/1999 | Barry et al. |
| 5,935,506 A | 8/1999 | Schmitz et al. |
| 5,938,903 A | 8/1999 | Broderick |
| 5,941,843 A | 8/1999 | Atanasoska et al. |
| 5,951,458 A | 9/1999 | Hastings et al. |
| 5,951,881 A | 9/1999 | Rogers et al. |
| 5,954,706 A | 9/1999 | Sahatjian |
| 5,957,975 A | 9/1999 | Lafont et al. |
| 5,958,440 A | 9/1999 | Burrell et al. |
| 5,961,547 A | 10/1999 | Razavi |
| 5,968,091 A | 10/1999 | Pinchuk et al. |
| 5,968,092 A | 10/1999 | Buscemi et al. |
| 5,972,027 A | 10/1999 | Johnson |
| 5,972,192 A | 10/1999 | Dubin et al. |
| 5,976,169 A | 11/1999 | Imran |

| Patent Number | Date | Inventor |
|---|---|---|
| 5,976,454 A | 11/1999 | Sterzel et al. |
| 5,977,204 A | 11/1999 | Boyan et al. |
| 5,980,554 A | 11/1999 | Lenker et al. |
| 5,980,564 A | 11/1999 | Stinson |
| 5,980,566 A * | 11/1999 | Alt et al. ................ 623/23.7 |
| 6,001,125 A | 12/1999 | Golds et al. |
| 6,013,591 A | 1/2000 | Ying et al. |
| 6,017,553 A | 1/2000 | Burrell et al. |
| 6,017,577 A | 1/2000 | Hostettler et al. |
| 6,021,347 A | 2/2000 | Herbst et al. |
| 6,025,036 A | 2/2000 | McGill et al. |
| 6,027,742 A | 2/2000 | Lee et al. |
| 6,034,295 A | 3/2000 | Rehberg et al. |
| 6,042,597 A | 3/2000 | Kveen et al. |
| 6,056,776 A | 5/2000 | Lau et al. |
| 6,063,101 A | 5/2000 | Jacobsen et al. |
| 6,071,305 A | 6/2000 | Brown et al. |
| 6,080,190 A | 6/2000 | Schwartz |
| 6,086,773 A | 7/2000 | Dufresne et al. |
| 6,096,070 A | 8/2000 | Ragheb et al. |
| 6,096,175 A | 8/2000 | Roth |
| 6,099,561 A | 8/2000 | Alt |
| 6,099,562 A | 8/2000 | Ding et al. |
| 6,106,473 A | 8/2000 | Violante et al. |
| 6,107,004 A | 8/2000 | Donadio, III |
| 6,117,592 A | 9/2000 | Hoshino et al. |
| 6,120,260 A | 9/2000 | Jirele |
| 6,120,535 A | 9/2000 | McDonald et al. |
| 6,120,660 A | 9/2000 | Chu et al. |
| 6,123,861 A | 9/2000 | Santini, Jr. et al. |
| 6,132,463 A | 10/2000 | Lee et al. |
| 6,139,573 A | 10/2000 | Sogard et al. |
| 6,139,574 A | 10/2000 | Vacanti et al. |
| 6,139,913 A | 10/2000 | Van Steenkiste et al. |
| 6,140,740 A | 10/2000 | Porat et al. |
| 6,143,370 A | 11/2000 | Panagiotou et al. |
| 6,153,252 A | 11/2000 | Hossainy et al. |
| 6,159,142 A | 12/2000 | Alt |
| 6,162,238 A | 12/2000 | Kaplan et al. |
| 6,164,284 A | 12/2000 | Schulman et al. |
| 6,165,211 A | 12/2000 | Thompson |
| 6,167,307 A | 12/2000 | Hess |
| 6,168,602 B1 | 1/2001 | Ryan |
| 6,170,488 B1 | 1/2001 | Spillman, Jr. et al. |
| 6,174,329 B1 | 1/2001 | Callol et al. |
| 6,174,330 B1 | 1/2001 | Stinson |
| 6,180,222 B1 | 1/2001 | Schulz et al. |
| 6,185,455 B1 | 2/2001 | Loeb et al. |
| 6,185,457 B1 | 2/2001 | Kroll et al. |
| 6,190,404 B1 | 2/2001 | Palmaz et al. |
| 6,192,271 B1 * | 2/2001 | Hayman .................... 604/21 |
| 6,201,991 B1 | 3/2001 | Chekanov |
| 6,203,536 B1 | 3/2001 | Berg et al. |
| 6,206,914 B1 | 3/2001 | Soykan et al. |
| 6,206,915 B1 | 3/2001 | Fagan et al. |
| 6,206,916 B1 | 3/2001 | Furst |
| 6,212,434 B1 | 4/2001 | Scheiner |
| 6,214,037 B1 | 4/2001 | Mitchell et al. |
| 6,214,042 B1 | 4/2001 | Jacobsen et al. |
| 6,217,607 B1 | 4/2001 | Alt |
| 6,231,597 B1 | 5/2001 | Deem et al. |
| 6,240,616 B1 | 6/2001 | Yan |
| 6,241,762 B1 | 6/2001 | Shanley |
| 6,245,103 B1 | 6/2001 | Stinson |
| 6,245,104 B1 | 6/2001 | Alt |
| 6,249,952 B1 | 6/2001 | Ding |
| 6,251,136 B1 | 6/2001 | Guruwaiya et al. |
| 6,251,980 B1 | 6/2001 | Lan et al. |
| 6,253,252 B1 | 6/2001 | Schofield |
| 6,253,443 B1 | 7/2001 | Johnson |
| 6,254,632 B1 | 7/2001 | Wu et al. |
| 6,258,117 B1 | 7/2001 | Camrud et al. |
| 6,264,687 B1 | 7/2001 | Tomonto |
| 6,270,831 B2 | 8/2001 | Kumar et al. |
| 6,273,908 B1 | 8/2001 | Ndondo-Lay |
| 6,273,913 B1 | 8/2001 | Wright et al. |
| 6,277,078 B1 | 8/2001 | Porat et al. |
| 6,280,385 B1 | 8/2001 | Melzer et al. |
| 6,280,411 B1 | 8/2001 | Lennox |
| 6,283,386 B1 | 9/2001 | Van Steenkiste et al. |
| 6,287,331 B1 | 9/2001 | Heath |
| 6,287,332 B1 | 9/2001 | Bolz et al. |
| 6,287,335 B1 * | 9/2001 | Drasler et al. ............... 623/1.28 |
| 6,287,628 B1 | 9/2001 | Hossainy et al. |
| 6,290,721 B1 | 9/2001 | Heath |
| 6,290,722 B1 | 9/2001 | Wang |
| 6,291,076 B1 | 9/2001 | Nakatsugawa |
| 6,299,604 B1 | 10/2001 | Ragheb et al. |
| 6,299,755 B1 | 10/2001 | Richter |
| 6,306,144 B1 | 10/2001 | Sydney et al. |
| 6,309,414 B1 | 10/2001 | Rolando et al. |
| 6,312,463 B1 | 11/2001 | Rourke et al. |
| 6,315,708 B1 | 11/2001 | Salmon et al. |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,312 B1 | 12/2001 | Lee et al. |
| 6,335,029 B1 | 1/2002 | Kamath et al. |
| 6,337,076 B1 | 1/2002 | Studin |
| 6,338,739 B1 | 1/2002 | Datta et al. |
| 6,342,507 B1 | 1/2002 | Naicker et al. |
| 6,344,055 B1 | 2/2002 | Shukov |
| 6,348,960 B1 | 2/2002 | Etori et al. |
| 6,358,276 B1 | 3/2002 | Edwin |
| 6,364,823 B1 | 4/2002 | Garibaldi et al. |
| 6,364,856 B1 | 4/2002 | Ding et al. |
| 6,364,903 B2 | 4/2002 | Tseng et al. |
| 6,366,808 B1 | 4/2002 | Schroeppel et al. |
| 6,368,658 B1 | 4/2002 | Schwarz et al. |
| 6,369,355 B1 | 4/2002 | Saunders |
| 6,375,826 B1 | 4/2002 | Wang et al. |
| 6,379,379 B1 | 4/2002 | Wang |
| 6,379,382 B1 | 4/2002 | Yang et al. |
| 6,379,383 B1 | 4/2002 | Palmaz et al. |
| 6,379,392 B1 | 4/2002 | Walak |
| 6,383,214 B1 | 5/2002 | Banas et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,033 B2 | 5/2002 | Ryan |
| 6,391,052 B2 | 5/2002 | Bulrge et al. |
| 6,395,326 B1 | 5/2002 | Castro et al. |
| 6,398,806 B1 | 6/2002 | You |
| 6,409,754 B1 | 6/2002 | Smith et al. |
| 6,419,692 B1 | 7/2002 | Yang et al. |
| 6,423,092 B2 | 7/2002 | Datta et al. |
| 6,425,855 B2 | 7/2002 | Tomonto |
| 6,436,133 B1 | 8/2002 | Furst et al. |
| 6,440,166 B1 | 8/2002 | Kolluri |
| 6,440,487 B1 | 8/2002 | Delfino et al. |
| 6,440,503 B1 | 8/2002 | Merdan et al. |
| 6,447,540 B1 | 9/2002 | Fontaine et al. |
| 6,451,871 B1 | 9/2002 | Winterton et al. |
| 6,458,153 B1 | 10/2002 | Bailey et al. |
| 6,468,304 B1 | 10/2002 | Dubois-Rande et al. |
| 6,471,721 B1 | 10/2002 | Dang |
| 6,471,980 B2 | 10/2002 | Sirhan et al. |
| 6,475,477 B1 | 11/2002 | Kohn et al. |
| 6,478,815 B1 | 11/2002 | Alt |
| 6,479,146 B1 | 11/2002 | Caruso et al. |
| 6,486,588 B2 | 11/2002 | Doron |
| 6,488,702 B1 | 12/2002 | Besselink |
| 6,491,666 B1 | 12/2002 | Santini, Jr. et al. |
| 6,491,720 B1 * | 12/2002 | Vallana et al. ............... 623/1.42 |
| 6,492,096 B1 | 12/2002 | Liu et al. |
| 6,503,556 B2 | 1/2003 | Harish et al. |
| 6,503,921 B2 | 1/2003 | Naicker et al. |
| 6,506,437 B1 | 1/2003 | Harish et al. |
| 6,506,972 B1 | 1/2003 | Wang |
| 6,514,283 B2 | 2/2003 | DiMatteo et al. |
| 6,517,571 B1 | 2/2003 | Brauker et al. |
| 6,517,888 B1 | 2/2003 | Weber |
| 6,524,274 B1 | 2/2003 | Rosenthal et al. |
| 6,524,334 B1 | 2/2003 | Thompson |
| 6,527,801 B1 | 3/2003 | Dutta |
| 6,527,938 B2 | 3/2003 | Bales et al. |
| 6,530,949 B2 | 3/2003 | Konya et al. |
| 6,530,951 B1 | 3/2003 | Bates et al. |

| | | |
|---|---|---|
| 6,537,310 B1 | 3/2003 | Palmaz et al. |
| 6,537,312 B2 | 3/2003 | Datta et al. |
| 6,544,582 B1 | 4/2003 | Yoe |
| 6,545,097 B2 | 4/2003 | Pinchuk et al. |
| 6,549,811 B2 | 4/2003 | Stewart et al. |
| 6,554,854 B1 | 4/2003 | Flanagan |
| 6,558,422 B1 | 5/2003 | Baker et al. |
| 6,569,489 B1 | 5/2003 | Li |
| 6,584,349 B1 | 6/2003 | Sage et al. |
| 6,585,764 B2 | 7/2003 | Wright et al. |
| 6,585,765 B1 | 7/2003 | Hossainy et al. |
| 6,586,705 B1 | 7/2003 | Schell |
| 6,589,286 B1 | 7/2003 | Litner |
| 6,599,558 B1 | 7/2003 | Al-Lamee et al. |
| 6,602,287 B1 | 8/2003 | Millare et al. |
| 6,607,598 B2 | 8/2003 | Schwarz et al. |
| 6,613,077 B2 | 9/2003 | Gilligan et al. |
| 6,613,083 B2 | 9/2003 | Alt |
| 6,613,432 B2 | 9/2003 | Zamora et al. |
| 6,616,765 B1 | 9/2003 | Castro et al. |
| 6,626,933 B1 | 9/2003 | Lau et al. |
| 6,626,936 B2 | 9/2003 | Stinson |
| 6,626,939 B1 | 9/2003 | Burnside et al. |
| 6,627,321 B1 | 9/2003 | Ellingsen et al. |
| 6,628,989 B1 | 9/2003 | Penner |
| 6,629,992 B2 | 10/2003 | Bigus et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,385 B1 | 1/2004 | Ding et al. |
| 6,673,999 B1 | 1/2004 | Wang et al. |
| 6,676,987 B2 | 1/2004 | Zhong et al. |
| 6,676,989 B2 | 1/2004 | Kirkpatrick et al. |
| 6,689,160 B1 | 2/2004 | Okuda et al. |
| 6,689,803 B2 | 2/2004 | Hunter |
| 6,695,865 B2 | 2/2004 | Boyle et al. |
| 6,696,666 B2 | 2/2004 | Merdan et al. |
| 6,696,667 B1 | 2/2004 | Flanagan |
| 6,699,281 B2 | 3/2004 | Vallana et al. |
| 6,699,282 B1 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,719,987 B2 | 4/2004 | Burrell et al. |
| 6,720,402 B2 | 4/2004 | Langer et al. |
| 6,723,120 B2 | 4/2004 | Yan |
| 6,723,350 B2 | 4/2004 | Burrell et al. |
| 6,725,901 B2 | 4/2004 | Kramer et al. |
| 6,726,712 B1 | 4/2004 | Raeder-Devens et al. |
| 6,730,117 B1 | 5/2004 | Tseng et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,740,077 B1 | 5/2004 | Brandau et al. |
| 6,743,388 B2 | 6/2004 | Sridharan et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,770,086 B1 | 8/2004 | Girton |
| 6,770,729 B2 | 8/2004 | Van Antwerp |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,776,793 B2 | 8/2004 | Brown et al. |
| 6,780,424 B2 | 8/2004 | Claude |
| 6,783,543 B2 | 8/2004 | Jang |
| 6,790,228 B2 | 9/2004 | Hossainy et al. |
| 6,793,877 B1 | 9/2004 | Pettersen et al. |
| 6,796,435 B2 | 9/2004 | Izumi |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| RE38,653 E | 11/2004 | Igaki et al. |
| 6,815,609 B1 | 11/2004 | Wang et al. |
| 6,820,676 B2 | 11/2004 | Palmaz et al. |
| 6,827,737 B2 | 12/2004 | Hill et al. |
| 6,827,966 B2 | 12/2004 | Qiu et al. |
| 6,833,004 B2 | 12/2004 | Ishii et al. |
| 6,846,323 B2 | 1/2005 | Yip et al. |
| 6,846,841 B2 | 1/2005 | Hunter et al. |
| 6,847,837 B1 | 1/2005 | Melzer et al. |
| 6,849,085 B2 | 2/2005 | Marton |
| 6,849,089 B2 | 2/2005 | Stoll |
| 6,852,122 B2 | 2/2005 | Rush |
| 6,854,172 B2 | 2/2005 | Kaese et al. |
| 6,861,088 B2 | 3/2005 | Weber et al. |
| 6,865,810 B2 | 3/2005 | Stinson |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,887,270 B2 | 5/2005 | Miller et al. |
| 6,887,857 B2 | 5/2005 | Naimark et al. |
| 6,896,697 B1 | 5/2005 | Yip et al. |
| 6,899,731 B2 | 5/2005 | Li et al. |
| 6,899,914 B2 | 5/2005 | Schaldach et al. |
| 6,904,658 B2 | 6/2005 | Hines |
| 6,908,506 B2 | 6/2005 | Zimmermann |
| 6,908,622 B2 | 6/2005 | Barry et al. |
| 6,908,624 B2 | 6/2005 | Hossainy et al. |
| 6,913,617 B1 | 7/2005 | Reiss |
| 6,913,765 B2 | 7/2005 | Li et al. |
| 6,918,869 B2 | 7/2005 | Shaw et al. |
| 6,918,927 B2 | 7/2005 | Bates et al. |
| 6,921,390 B2 | 7/2005 | Bucay-Couto et al. |
| 6,923,996 B2 | 8/2005 | Epstein et al. |
| 6,926,735 B2 | 8/2005 | Henderson |
| 6,932,930 B2 | 8/2005 | DeSimone et al. |
| 6,936,066 B2 | 8/2005 | Palmaz et al. |
| 6,939,320 B2 | 9/2005 | Lennox |
| 6,945,993 B2 | 9/2005 | Kveen et al. |
| 6,951,053 B2 | 10/2005 | Padilla et al. |
| 6,953,560 B1 | 10/2005 | Castro et al. |
| 6,953,594 B2 | 10/2005 | Lee et al. |
| 6,954,977 B2 | 10/2005 | Maguire et al. |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,964,817 B2 | 11/2005 | Date et al. |
| 6,971,813 B2 | 12/2005 | Shekalim et al. |
| 6,972,130 B1 | 12/2005 | Lee et al. |
| 6,973,718 B2 | 12/2005 | Sheppard, Jr. et al. |
| 6,979,346 B1 | 12/2005 | Hossainy et al. |
| 6,979,347 B1 * | 12/2005 | Wu et al. ..................... 623/1.15 |
| 6,979,348 B2 | 12/2005 | Sundar |
| 6,981,986 B1 | 1/2006 | Brown et al. |
| 6,984,404 B1 | 1/2006 | Talton et al. |
| 6,986,899 B2 | 1/2006 | Hossainy et al. |
| 6,989,156 B2 | 1/2006 | Gillis |
| 6,991,709 B2 | 1/2006 | Gopalraja et al. |
| 7,001,421 B2 | 2/2006 | Cheng et al. |
| 7,004,968 B2 | 2/2006 | Lootz et al. |
| 7,011,670 B2 | 3/2006 | Radisch, Jr. |
| 7,011,678 B2 | 3/2006 | Tenerz et al. |
| 7,011,680 B2 | 3/2006 | Alt |

| Patent/Pub. No. | Date | Inventor |
|---|---|---|
| 7,018,408 B2 | 3/2006 | Bailey et al. |
| 7,022,334 B1 | 4/2006 | Ding et al. |
| 7,041,130 B2 | 5/2006 | Santini, Jr. et al. |
| 7,048,767 B2 | 5/2006 | Namavar |
| 7,048,939 B2 | 5/2006 | Elkins et al. |
| 7,052,488 B2 | 5/2006 | Uhland |
| 7,056,338 B2 | 6/2006 | Shanley et al. |
| 7,056,339 B2 | 6/2006 | Elkins et al. |
| 7,060,051 B2 | 6/2006 | Palasis |
| 7,060,240 B2 | 6/2006 | Costa et al. |
| 7,063,748 B2 | 6/2006 | Talton |
| 7,067,606 B2 | 6/2006 | Mather et al. |
| 7,070,576 B2 | 7/2006 | O'Brien et al. |
| 7,077,859 B2 | 7/2006 | Sirhan et al. |
| 7,078,108 B2 | 7/2006 | Zhang et al. |
| 7,099,091 B2 | 8/2006 | Taniguchi et al. |
| 7,101,391 B2 | 9/2006 | Scheuermann et al. |
| 7,101,394 B2 | 9/2006 | Hamm et al. |
| 7,105,018 B1 | 9/2006 | Yip et al. |
| 7,105,199 B2 | 9/2006 | Blinn et al. |
| 7,108,716 B2 | 9/2006 | Burnside et al. |
| 7,157,096 B2 | 1/2007 | Zhang et al. |
| 7,160,592 B2 | 1/2007 | Rypacek et al. |
| 7,163,715 B1 | 1/2007 | Kramer |
| 7,169,173 B2 | 1/2007 | Hossainy et al. |
| 7,169,178 B1 | 1/2007 | Santos et al. |
| 7,195,640 B2 | 3/2007 | Falotico et al. |
| 7,195,641 B2 | 3/2007 | Palmaz et al. |
| 7,198,675 B2 | 4/2007 | Fox et al. |
| 7,208,011 B2 | 4/2007 | Shanley et al. |
| 7,208,172 B2 | 4/2007 | Birdsall et al. |
| 7,220,816 B2 | 5/2007 | Pacetti |
| 7,226,475 B2 | 6/2007 | Lenz et al. |
| 7,229,471 B2 | 6/2007 | Gale et al. |
| 7,235,096 B1 | 6/2007 | Van Tassel et al. |
| 7,235,098 B2 | 6/2007 | Palmaz |
| 7,238,199 B2 | 7/2007 | Feldman et al. |
| 7,241,295 B2 | 7/2007 | Maguire |
| 7,244,272 B2 | 7/2007 | Dubson et al. |
| 7,261,732 B2 | 8/2007 | Justino |
| 7,261,735 B2 | 8/2007 | Llanos et al. |
| 7,267,960 B2 | 9/2007 | Galibert et al. |
| 7,279,174 B2 | 10/2007 | Pacetti |
| 7,279,175 B2 | 10/2007 | Chen |
| 7,294,409 B2 | 11/2007 | Lye et al. |
| 7,311,727 B2 | 12/2007 | Mazumder et al. |
| 7,323,189 B2 | 1/2008 | Pathak |
| RE40,122 E | 2/2008 | Thompson |
| 7,331,993 B2 | 2/2008 | White |
| 7,335,375 B2 | 2/2008 | Li et al. |
| 7,344,560 B2 | 3/2008 | Gregorich et al. |
| 7,344,563 B2 | 3/2008 | Vallana et al. |
| 7,393,589 B2 | 7/2008 | Aharonov et al. |
| 7,402,173 B2 | 7/2008 | Scheuermann et al. |
| 7,416,558 B2 | 8/2008 | Yip et al. |
| 7,432,327 B2 | 10/2008 | Glasgow et al. |
| 7,462,366 B2 | 12/2008 | Lanphere |
| 7,498,385 B2 | 3/2009 | Swetlin et al. |
| 7,507,433 B2 | 3/2009 | Weber |
| 7,537,610 B2 | 5/2009 | Reiss |
| 7,547,445 B2 | 6/2009 | Chudzik et al. |
| 7,563,277 B2 | 7/2009 | Case et al. |
| 7,637,941 B1 | 12/2009 | Manicka et al. |
| 7,651,527 B2 | 1/2010 | Krivoruchko et al. |
| 7,691,401 B2 | 4/2010 | Castro et al. |
| 7,713,297 B2 | 5/2010 | Alt |
| 7,749,264 B2 | 7/2010 | Gregorich et al. |
| 7,758,635 B2 | 7/2010 | Parsonage |
| 7,771,773 B2 | 8/2010 | Namavar |
| 7,776,926 B1 | 8/2010 | Claude et al. |
| 2001/0001834 A1 | 5/2001 | Palmaz et al. |
| 2001/0002000 A1 | 5/2001 | Kumar et al. |
| 2001/0002435 A1 | 5/2001 | Berg et al. |
| 2001/0013166 A1 | 8/2001 | Yan |
| 2001/0021871 A1 | 9/2001 | Stinson |
| 2001/0021873 A1* | 9/2001 | Stinson ............ 623/1.34 |
| 2001/0027299 A1 | 10/2001 | Yang et al. |
| 2001/0029398 A1 | 10/2001 | Jadhav |
| 2001/0029660 A1 | 10/2001 | Johnson |
| 2001/0032011 A1 | 10/2001 | Stanford |
| 2001/0032013 A1 | 10/2001 | Marton |
| 2001/0032014 A1 | 10/2001 | Yang et al. |
| 2001/0044650 A1 | 11/2001 | Simso et al. |
| 2002/0000175 A1 | 1/2002 | Hintermaier et al. |
| 2002/0000406 A1 | 1/2002 | Izumi |
| 2002/0004060 A1 | 1/2002 | Heublein et al. |
| 2002/0007102 A1 | 1/2002 | Salmon et al. |
| 2002/0007209 A1 | 1/2002 | Schearder et al. |
| 2002/0010505 A1 | 1/2002 | Richter |
| 2002/0016623 A1 | 2/2002 | Kula et al. |
| 2002/0016624 A1 | 2/2002 | Patterson et al. |
| 2002/0028827 A1 | 3/2002 | Naicker et al. |
| 2002/0032477 A1 | 3/2002 | Helmus et al. |
| 2002/0035394 A1 | 3/2002 | Fierens et al. |
| 2002/0038146 A1 | 3/2002 | Harry |
| 2002/0042039 A1 | 4/2002 | Kim et al. |
| 2002/0049495 A1 | 4/2002 | Kutryk et al. |
| 2002/0051730 A1 | 5/2002 | Bodnar et al. |
| 2002/0051846 A1 | 5/2002 | Kirkpatrick et al. |
| 2002/0065553 A1 | 5/2002 | Weber |
| 2002/0082679 A1 | 6/2002 | Sirhan et al. |
| 2002/0087123 A1 | 7/2002 | Hossainy et al. |
| 2002/0090313 A1 | 7/2002 | Wang et al. |
| 2002/0091375 A1 | 7/2002 | Sahatjian et al. |
| 2002/0098278 A1 | 7/2002 | Bates et al. |
| 2002/0099434 A1 | 7/2002 | Buscemi et al. |
| 2002/0099438 A1 | 7/2002 | Furst |
| 2002/0103527 A1 | 8/2002 | Kocur et al. |
| 2002/0103528 A1 | 8/2002 | Schaldach et al. |
| 2002/0111694 A1 | 8/2002 | Ellingsen et al. |
| 2002/0121497 A1 | 9/2002 | Tomonto |
| 2002/0123801 A1 | 9/2002 | Pacetti et al. |
| 2002/0133222 A1 | 9/2002 | Das |
| 2002/0133224 A1 | 9/2002 | Bajgar et al. |
| 2002/0138100 A1 | 9/2002 | Stoll et al. |
| 2002/0138131 A1 | 9/2002 | Solovay et al. |
| 2002/0138136 A1 | 9/2002 | Chandresekaran et al. |
| 2002/0138154 A1 | 9/2002 | Li et al. |
| 2002/0144757 A1 | 10/2002 | Craig et al. |
| 2002/0151964 A1 | 10/2002 | Smith et al. |
| 2002/0155212 A1 | 10/2002 | Hossainy |
| 2002/0165265 A1 | 11/2002 | Hunter et al. |
| 2002/0165578 A1 | 11/2002 | Sawitowski et al. |
| 2002/0165600 A1 | 11/2002 | Banas et al. |
| 2002/0165607 A1 | 11/2002 | Alt |
| 2002/0169493 A1 | 11/2002 | Widenhouse et al. |
| 2002/0178570 A1 | 12/2002 | Sogard et al. |
| 2002/0182241 A1 | 12/2002 | Borenstein et al. |
| 2002/0183581 A1 | 12/2002 | Yoe et al. |
| 2002/0187260 A1 | 12/2002 | Sheppard, Jr. et al. |
| 2002/0193336 A1 | 12/2002 | Elkins et al. |
| 2002/0193682 A1 | 12/2002 | Torchia et al. |
| 2002/0193869 A1 | 12/2002 | Dang |
| 2002/0197178 A1 | 12/2002 | Yan |
| 2002/0198601 A1 | 12/2002 | Bales et al. |
| 2003/0003127 A1 | 1/2003 | Brown et al. |
| 2003/0003220 A1 | 1/2003 | Zhong et al. |
| 2003/0004563 A1 | 1/2003 | Jackson et al. |
| 2003/0004564 A1 | 1/2003 | Elkins et al. |
| 2003/0009214 A1 | 1/2003 | Shanley |
| 2003/0018380 A1 | 1/2003 | Craig et al. |
| 2003/0018381 A1 | 1/2003 | Whitcher et al. |
| 2003/0023300 A1 | 1/2003 | Bailey et al. |
| 2003/0028242 A1 | 2/2003 | Vallana et al. |
| 2003/0028243 A1 | 2/2003 | Bates et al. |
| 2003/0032892 A1 | 2/2003 | Erlach et al. |
| 2003/0033007 A1 | 2/2003 | Sirhan et al. |
| 2003/0044446 A1 | 3/2003 | Moro et al. |
| 2003/0044596 A1 | 3/2003 | Lazarov et al. |
| 2003/0050687 A1 | 3/2003 | Schwade et al. |
| 2003/0050692 A1 | 3/2003 | Sirhan et al. |
| 2003/0059640 A1 | 3/2003 | Marton et al. |
| 2003/0060871 A1 | 3/2003 | Hill et al. |
| 2003/0060873 A1 | 3/2003 | Gertner et al. |
| 2003/0064095 A1 | 4/2003 | Martin et al. |
| 2003/0068355 A1 | 4/2003 | Shanley et al. |
| 2003/0069631 A1 | 4/2003 | Stoll |
| 2003/0074053 A1 | 4/2003 | Palmaz et al. |

| | | | |
|---|---|---|---|
| 2003/0077200 A1 | 4/2003 | Craig et al. | |
| 2003/0077310 A1 | 4/2003 | Pathak et al. | |
| 2003/0083614 A1 | 5/2003 | Eisert | |
| 2003/0083646 A1 | 5/2003 | Sirhan et al. | |
| 2003/0083731 A1 | 5/2003 | Kramer et al. | |
| 2003/0087024 A1 | 5/2003 | Flanagan | |
| 2003/0088307 A1 | 5/2003 | Shulze et al. | |
| 2003/0088312 A1 | 5/2003 | Kopia et al. | |
| 2003/0099684 A1 | 5/2003 | Domb | |
| 2003/0100815 A1 | 5/2003 | Da Silva et al. | |
| 2003/0100830 A1 | 5/2003 | Zhong et al. | |
| 2003/0104030 A1 | 6/2003 | Igaki et al. | |
| 2003/0105511 A1 | 6/2003 | Welsh et al. | |
| 2003/0108659 A1 | 6/2003 | Bales et al. | |
| 2003/0114917 A1 | 6/2003 | Holloway et al. | |
| 2003/0114921 A1 | 6/2003 | Yoon | |
| 2003/0118692 A1 | 6/2003 | Wang et al. | |
| 2003/0120339 A1 | 6/2003 | Banik et al. | |
| 2003/0124055 A1 | 7/2003 | Li et al. | |
| 2003/0125803 A1 | 7/2003 | Vallana et al. | |
| 2003/0130718 A1 | 7/2003 | Palmas et al. | |
| 2003/0139799 A1 | 7/2003 | Ley et al. | |
| 2003/0143330 A1 | 7/2003 | Loomis et al. | |
| 2003/0144728 A1 | 7/2003 | Scheuermann et al. | |
| 2003/0150380 A1 | 8/2003 | Yoe | |
| 2003/0153901 A1 | 8/2003 | Herweck et al. | |
| 2003/0158598 A1 | 8/2003 | Ashton et al. | |
| 2003/0170605 A1 | 9/2003 | Long et al. | |
| 2003/0181975 A1 | 9/2003 | Ishii et al. | |
| 2003/0185895 A1 | 10/2003 | Lanphere et al. | |
| 2003/0190406 A1 | 10/2003 | Hossainy et al. | |
| 2003/0195613 A1 | 10/2003 | Curcio et al. | |
| 2003/0199993 A1 | 10/2003 | Gellman et al. | |
| 2003/0204239 A1 | 10/2003 | Carlyle et al. | |
| 2003/0211135 A1 | 11/2003 | Greenhalgh et al. | |
| 2003/0216803 A1 | 11/2003 | Ledergerber | |
| 2003/0219562 A1 | 11/2003 | Rypacek et al. | |
| 2003/0221307 A1 | 12/2003 | Kaese et al. | |
| 2003/0228523 A1 | 12/2003 | DeLongchamp et al. | |
| 2003/0236513 A1 | 12/2003 | Schwarz et al. | |
| 2004/0000046 A1 | 1/2004 | Stinson | |
| 2004/0000540 A1 | 1/2004 | Soboyejo et al. | |
| 2004/0004063 A1 | 1/2004 | Merdan | |
| 2004/0006382 A1 | 1/2004 | Sohier | |
| 2004/0018296 A1 | 1/2004 | Castro et al. | |
| 2004/0019376 A1 | 1/2004 | Alt | |
| 2004/0022939 A1 | 2/2004 | Kim et al. | |
| 2004/0024448 A1 | 2/2004 | Chang et al. | |
| 2004/0029303 A1 | 2/2004 | Hart et al. | |
| 2004/0030218 A1 | 2/2004 | Kocur et al. | |
| 2004/0030377 A1 | 2/2004 | Dubson et al. | |
| 2004/0030379 A1 | 2/2004 | Hamm et al. | |
| 2004/0034409 A1 | 2/2004 | Heublein et al. | |
| 2004/0039438 A1* | 2/2004 | Alt | 623/1.15 |
| 2004/0039441 A1 | 2/2004 | Rowland et al. | |
| 2004/0044397 A1 | 3/2004 | Stinson | |
| 2004/0047980 A1 | 3/2004 | Pacetti et al. | |
| 2004/0059407 A1 | 3/2004 | Escamilla et al. | |
| 2004/0059409 A1 | 3/2004 | Stenzel | |
| 2004/0067301 A1 | 4/2004 | Ding | |
| 2004/0071861 A1 | 4/2004 | Mandrusov et al. | |
| 2004/0073155 A1 | 4/2004 | Laufer et al. | |
| 2004/0073284 A1 | 4/2004 | Bates et al. | |
| 2004/0073293 A1* | 4/2004 | Thompson | 623/1.19 |
| 2004/0073297 A1 | 4/2004 | Rohde et al. | |
| 2004/0073298 A1 | 4/2004 | Hossainy | |
| 2004/0078071 A1 | 4/2004 | Escamilla et al. | |
| 2004/0082682 A1 | 4/2004 | Loomis et al. | |
| 2004/0088038 A1 | 5/2004 | Dehnad et al. | |
| 2004/0088041 A1 | 5/2004 | Stanford | |
| 2004/0093071 A1 | 5/2004 | Jang | |
| 2004/0093075 A1 | 5/2004 | Kuehne | |
| 2004/0093076 A1 | 5/2004 | White et al. | |
| 2004/0098089 A1 | 5/2004 | Weber | |
| 2004/0098108 A1 | 5/2004 | Harder et al. | |
| 2004/0098119 A1 | 5/2004 | Wang | |
| 2004/0106975 A1* | 6/2004 | Solovay et al. | 623/1.11 |
| 2004/0106984 A1 | 6/2004 | Stinson | |
| 2004/0106985 A1 | 6/2004 | Jang | |
| 2004/0111150 A1 | 6/2004 | Berg et al. | |
| 2004/0116999 A1 | 6/2004 | Ledergerber | |
| 2004/0117005 A1 | 6/2004 | Gadde et al. | |
| 2004/0117008 A1 | 6/2004 | Wnendt et al. | |
| 2004/0122504 A1 | 6/2004 | Hogendijk | |
| 2004/0126566 A1 | 7/2004 | Axen et al. | |
| 2004/0133270 A1 | 7/2004 | Grandt | |
| 2004/0134886 A1 | 7/2004 | Wagner et al. | |
| 2004/0137039 A1 | 7/2004 | Sukhishvili et al. | |
| 2004/0138738 A1 | 7/2004 | Stinson | |
| 2004/0142014 A1 | 7/2004 | Litvack et al. | |
| 2004/0143317 A1 | 7/2004 | Stinson et al. | |
| 2004/0143321 A1 | 7/2004 | Litvack et al. | |
| 2004/0148010 A1 | 7/2004 | Rush | |
| 2004/0148015 A1 | 7/2004 | Lye et al. | |
| 2004/0153138 A1 | 8/2004 | Murphy | |
| 2004/0157073 A1 | 8/2004 | Burrell et al. | |
| 2004/0158308 A1 | 8/2004 | Hogendijk et al. | |
| 2004/0158310 A1 | 8/2004 | Weber et al. | |
| 2004/0167572 A1 | 8/2004 | Roth et al. | |
| 2004/0167609 A1 | 8/2004 | Majercak | |
| 2004/0167612 A1 | 8/2004 | Grignani et al. | |
| 2004/0172124 A1 | 9/2004 | Vallana et al. | |
| 2004/0181252 A1 | 9/2004 | Boyle et al. | |
| 2004/0181275 A1 | 9/2004 | Noble et al. | |
| 2004/0181276 A1 | 9/2004 | Brown et al. | |
| 2004/0181278 A1 | 9/2004 | Tseng et al. | |
| 2004/0182511 A1 | 9/2004 | Rakos et al. | |
| 2004/0186553 A1 | 9/2004 | Yan | |
| 2004/0191293 A1 | 9/2004 | Claude | |
| 2004/0191404 A1 | 9/2004 | Hossainy et al. | |
| 2004/0202692 A1 | 10/2004 | Shanley et al. | |
| 2004/0204750 A1 | 10/2004 | Dinh | |
| 2004/0211362 A1 | 10/2004 | Castro et al. | |
| 2004/0219214 A1 | 11/2004 | Gravett et al. | |
| 2004/0220510 A1 | 11/2004 | Koullick et al. | |
| 2004/0220659 A1 | 11/2004 | Girton | |
| 2004/0220660 A1 | 11/2004 | Shanley et al. | |
| 2004/0220662 A1 | 11/2004 | Dang et al. | |
| 2004/0224001 A1 | 11/2004 | Pacetti et al. | |
| 2004/0225346 A1 | 11/2004 | Mazumder et al. | |
| 2004/0228905 A1 | 11/2004 | Greenspan et al. | |
| 2004/0230176 A1 | 11/2004 | Shanahan et al. | |
| 2004/0230225 A1 | 11/2004 | Penner et al. | |
| 2004/0230290 A1 | 11/2004 | Weber et al. | |
| 2004/0230293 A1 | 11/2004 | Yip et al. | |
| 2004/0234737 A1 | 11/2004 | Pacetti | |
| 2004/0236415 A1 | 11/2004 | Thomas | |
| 2004/0236416 A1 | 11/2004 | Falotico | |
| 2004/0237282 A1 | 12/2004 | Hines | |
| 2004/0242106 A1 | 12/2004 | Rabasco et al. | |
| 2004/0243217 A1 | 12/2004 | Andersen | |
| 2004/0243237 A1 | 12/2004 | Unwin et al. | |
| 2004/0243241 A1 | 12/2004 | Istephanous | |
| 2004/0247671 A1 | 12/2004 | Prescott et al. | |
| 2004/0249440 A1 | 12/2004 | Bucker et al. | |
| 2004/0249443 A1 | 12/2004 | Shanley et al. | |
| 2004/0249444 A1 | 12/2004 | Reiss | |
| 2004/0249445 A1* | 12/2004 | Rosenthal et al. | 623/1.15 |
| 2004/0249449 A1 | 12/2004 | Shanley et al. | |
| 2004/0254419 A1 | 12/2004 | Wang et al. | |
| 2004/0254635 A1 | 12/2004 | Shanley et al. | |
| 2005/0004661 A1 | 1/2005 | Lewis et al. | |
| 2005/0010275 A1 | 1/2005 | Sahatjian et al. | |
| 2005/0010279 A1 | 1/2005 | Tenerz et al. | |
| 2005/0015142 A1 | 1/2005 | Austin et al. | |
| 2005/0019265 A1 | 1/2005 | Hammer et al. | |
| 2005/0019371 A1 | 1/2005 | Anderson et al. | |
| 2005/0021127 A1 | 1/2005 | Kawula | |
| 2005/0021128 A1 | 1/2005 | Nakahama et al. | |
| 2005/0022627 A1 | 2/2005 | Chen | |
| 2005/0025804 A1 | 2/2005 | Heller | |
| 2005/0027350 A1 | 2/2005 | Momma et al. | |
| 2005/0033407 A1 | 2/2005 | Weber et al. | |
| 2005/0033411 A1 | 2/2005 | Wu et al. | |
| 2005/0033412 A1 | 2/2005 | Wu et al. | |
| 2005/0033417 A1 | 2/2005 | Borges et al. | |
| 2005/0037047 A1 | 2/2005 | Song | |
| 2005/0037050 A1 | 2/2005 | Weber | |

| | | | | | | |
|---|---|---|---|---|---|---|
| 2005/0038134 A1 | 2/2005 | Loomis et al. | 2005/0220853 A1 | 10/2005 | Dao et al. | |
| 2005/0038501 A1 | 2/2005 | Moore, Jr. et al. | 2005/0221072 A1 | 10/2005 | Dubrow et al. | |
| 2005/0042288 A1 | 2/2005 | Koblish et al. | 2005/0222671 A1 | 10/2005 | Schaeffer et al. | |
| 2005/0042440 A1 | 2/2005 | Bach et al. | 2005/0228477 A1 | 10/2005 | Grainger et al. | |
| 2005/0055044 A1 | 3/2005 | Kangas | 2005/0228483 A1 | 10/2005 | Kaplan et al. | |
| 2005/0055080 A1 | 3/2005 | Istephanous et al. | 2005/0228491 A1 | 10/2005 | Snyder et al. | |
| 2005/0055085 A1 | 3/2005 | Rivron et al. | 2005/0232968 A1 | 10/2005 | Palmaz et al. | |
| 2005/0060020 A1 | 3/2005 | Jenson | 2005/0233965 A1 | 10/2005 | Schwartz et al. | |
| 2005/0060021 A1 | 3/2005 | O'Brien et al. | 2005/0234538 A1 | 10/2005 | Litvack et al. | |
| 2005/0064088 A1 | 3/2005 | Fredrickson | 2005/0240280 A1 | 10/2005 | Aliski et al. | |
| 2005/0069630 A1 | 3/2005 | Fox et al. | 2005/0244459 A1 | 11/2005 | DeWitt et al. | |
| 2005/0070989 A1 | 3/2005 | Lye et al. | 2005/0251245 A1 | 11/2005 | Sieradzki et al. | |
| 2005/0070990 A1 | 3/2005 | Stinson | 2005/0251249 A1 | 11/2005 | Sahatjian et al. | |
| 2005/0070996 A1 | 3/2005 | Dinh et al. | 2005/0252893 A1 | 11/2005 | Shapovalov et al. | |
| 2005/0071016 A1 | 3/2005 | Hausdorf et al. | 2005/0255707 A1 | 11/2005 | Hart et al. | |
| 2005/0072544 A1 | 4/2005 | Palmaz et al. | 2005/0261760 A1 | 11/2005 | Weber | |
| 2005/0074479 A1 | 4/2005 | Weber et al. | 2005/0266039 A1 | 12/2005 | Weber | |
| 2005/0074545 A1 | 4/2005 | Thomas | 2005/0266040 A1 | 12/2005 | Gerberding | |
| 2005/0075714 A1 | 4/2005 | Cheng et al. | 2005/0266041 A1 | 12/2005 | Gerold et al. | |
| 2005/0077305 A1 | 4/2005 | Guevara | 2005/0267560 A1 | 12/2005 | Bates et al. | |
| 2005/0079132 A1 | 4/2005 | Wang et al. | 2005/0267561 A1 | 12/2005 | Jones et al. | |
| 2005/0079199 A1 | 4/2005 | Heruth et al. | 2005/0271703 A1 | 12/2005 | Anderson et al. | |
| 2005/0079356 A1 | 4/2005 | Rathenow et al. | 2005/0271706 A1 | 12/2005 | Anderson et al. | |
| 2005/0092615 A1 | 5/2005 | Birdsall et al. | 2005/0276837 A1 | 12/2005 | Anderson et al. | |
| 2005/0096731 A1 | 5/2005 | Looi et al. | 2005/0278016 A1 | 12/2005 | Welsh et al. | |
| 2005/0100577 A1 | 5/2005 | Parker et al. | 2005/0278021 A1 | 12/2005 | Bates et al. | |
| 2005/0100609 A1 | 5/2005 | Claude | 2005/0281863 A1 | 12/2005 | Anderson et al. | |
| 2005/0102025 A1 | 5/2005 | Laroche et al. | 2005/0283224 A1 | 12/2005 | King | |
| 2005/0106212 A1 | 5/2005 | Gertner et al. | 2005/0283229 A1 | 12/2005 | Dugan et al. | |
| 2005/0107869 A1 | 5/2005 | Sirhan et al. | 2005/0287188 A1 | 12/2005 | Anderson et al. | |
| 2005/0107870 A1 | 5/2005 | Wang et al. | 2006/0002979 A1 | 1/2006 | Ashammakhi et al. | |
| 2005/0113936 A1 | 5/2005 | Brustad et al. | 2006/0009798 A1* | 1/2006 | Callister et al. | 606/200 |
| 2005/0119723 A1 | 6/2005 | Peacock | 2006/0009839 A1 | 1/2006 | Tan | |
| 2005/0129727 A1* | 6/2005 | Weber et al. ............... 424/423 | 2006/0013850 A1 | 1/2006 | Domb | |
| 2005/0129731 A1 | 6/2005 | Horres et al. | 2006/0014039 A1 | 1/2006 | Zhang et al. | |
| 2005/0131509 A1 | 6/2005 | Atanasoska et al. | 2006/0015175 A1 | 1/2006 | Palmaz et al. | |
| 2005/0131521 A1 | 6/2005 | Marton | 2006/0015361 A1 | 1/2006 | Sattler et al. | |
| 2005/0131522 A1 | 6/2005 | Stinson et al. | 2006/0020742 A1 | 1/2006 | Au et al. | |
| 2005/0131527 A1 | 6/2005 | Pathak | 2006/0025848 A1 | 2/2006 | Weber et al. | |
| 2005/0131528 A1 | 6/2005 | Buscemi et al. | 2006/0035026 A1 | 2/2006 | Atanasoska et al. | |
| 2005/0136090 A1 | 6/2005 | Falotico et al. | 2006/0036281 A1* | 2/2006 | Patterson et al. | 606/200 |
| 2005/0137677 A1 | 6/2005 | Rush | 2006/0036311 A1 | 2/2006 | Nakayama et al. | |
| 2005/0137679 A1 | 6/2005 | Changelian et al. | 2006/0038027 A1 | 2/2006 | O'Connor et al. | |
| 2005/0137684 A1 | 6/2005 | Changelian et al. | 2006/0040388 A1 | 2/2006 | Bromberg et al. | |
| 2005/0149169 A1 | 7/2005 | Wang et al. | 2006/0041182 A1 | 2/2006 | Forbes et al. | |
| 2005/0149170 A1 | 7/2005 | Tassel et al. | 2006/0051397 A1 | 3/2006 | Maier et al. | |
| 2005/0149175 A1 | 7/2005 | Hunter et al. | 2006/0052744 A1 | 3/2006 | Weber | |
| 2005/0149177 A1 | 7/2005 | Weber et al. | 2006/0052863 A1 | 3/2006 | Harder et al. | |
| 2005/0159804 A1 | 7/2005 | Lad et al. | 2006/0052864 A1 | 3/2006 | Harder et al. | |
| 2005/0159805 A1 | 7/2005 | Weber et al. | 2006/0058868 A1 | 3/2006 | Gale et al. | |
| 2005/0159809 A1 | 7/2005 | Hezi-Yamit et al. | 2006/0062820 A1 | 3/2006 | Gertner et al. | |
| 2005/0160600 A1 | 7/2005 | Bien et al. | 2006/0064160 A1 | 3/2006 | Gerold et al. | |
| 2005/0163821 A1 | 7/2005 | Sung et al. | 2006/0067908 A1 | 3/2006 | Ding | |
| 2005/0163954 A1 | 7/2005 | Shaw | 2006/0069427 A1 | 3/2006 | Savage et al. | |
| 2005/0165301 A1 | 7/2005 | Smith et al. | 2006/0075044 A1 | 4/2006 | Fox et al. | |
| 2005/0165468 A1 | 7/2005 | Marton | 2006/0075092 A1 | 4/2006 | Kidokoro | |
| 2005/0165470 A1 | 7/2005 | Weber | 2006/0079958 A1 | 4/2006 | Stratford et al. | |
| 2005/0169969 A1 | 8/2005 | Li et al. | 2006/0085062 A1 | 4/2006 | Lee et al. | |
| 2005/0171595 A1 | 8/2005 | Feldman et al. | 2006/0085065 A1 | 4/2006 | Krause et al. | |
| 2005/0177226 A1 | 8/2005 | Banik et al. | 2006/0088566 A1 | 4/2006 | Parsonage et al. | |
| 2005/0180919 A1 | 8/2005 | Tedeschi | 2006/0088567 A1 | 4/2006 | Warner et al. | |
| 2005/0182361 A1 | 8/2005 | Lennox | 2006/0088653 A1 | 4/2006 | Chappa et al. | |
| 2005/0182478 A1 | 8/2005 | Holman et al. | 2006/0088666 A1 | 4/2006 | Kobrin et al. | |
| 2005/0186250 A1 | 8/2005 | Gertner et al. | 2006/0100696 A1 | 5/2006 | Atanasoska et al. | |
| 2005/0187605 A1 | 8/2005 | Greenhalgh et al. | 2006/0115512 A1 | 6/2006 | Peacock et al. | |
| 2005/0187611 A1 | 8/2005 | Ding et al. | 2006/0118236 A1 | 6/2006 | House et al. | |
| 2005/0187615 A1 | 8/2005 | Williams et al. | 2006/0121080 A1 | 6/2006 | Lye et al. | |
| 2005/0192657 A1 | 9/2005 | Colen et al. | 2006/0122694 A1 | 6/2006 | Stinson et al. | |
| 2005/0192662 A1 | 9/2005 | Ward | 2006/0122697 A1 | 6/2006 | Shanley et al. | |
| 2005/0192664 A1 | 9/2005 | Eisert | 2006/0124472 A1 | 6/2006 | Rokicki | |
| 2005/0196424 A1 | 9/2005 | Chappa | 2006/0127266 A1 | 6/2006 | Miura et al. | |
| 2005/0208098 A1 | 9/2005 | Castro et al. | 2006/0129215 A1 | 6/2006 | Helmus et al. | |
| 2005/0208100 A1 | 9/2005 | Weber et al. | 2006/0129222 A1 | 6/2006 | Stinson | |
| 2005/0209680 A1 | 9/2005 | Gale et al. | 2006/0129225 A1 | 6/2006 | Kopia et al. | |
| 2005/0209681 A1 | 9/2005 | Curcio et al. | 2006/0136048 A1 | 6/2006 | Pacetti et al. | |
| 2005/0211680 A1 | 9/2005 | Li et al. | 2006/0136051 A1 | 6/2006 | Furst et al. | |
| 2005/0214951 A1 | 9/2005 | Nahm et al. | 2006/0141156 A1 | 6/2006 | Viel et al. | |
| 2005/0216074 A1 | 9/2005 | Sahatjian et al. | 2006/0149352 A1 | 7/2006 | Schlun | |
| 2005/0216075 A1 | 9/2005 | Wang et al. | 2006/0153729 A1 | 7/2006 | Stinson et al. | |

| | | | | | | |
|---|---|---|---|---|---|---|
| 2006/0155361 A1 | 7/2006 | Schomig et al. | | 2007/0134288 A1 | 6/2007 | Parsonage et al. |
| 2006/0167543 A1 | 7/2006 | Bailey et al. | | 2007/0135908 A1 | 6/2007 | Zhao |
| 2006/0177480 A1 | 8/2006 | Sung et al. | | 2007/0141106 A1 | 6/2007 | Bonutti et al. |
| 2006/0178727 A1 | 8/2006 | Richter | | 2007/0142897 A1 | 6/2007 | Consigny et al. |
| 2006/0184235 A1 | 8/2006 | Rivron et al. | | 2007/0142899 A1 | 6/2007 | Lootz et al. |
| 2006/0193886 A1 | 8/2006 | Owens et al. | | 2007/0148251 A1 | 6/2007 | Hossainy et al. |
| 2006/0193887 A1 | 8/2006 | Owens et al. | | 2007/0151093 A1 | 7/2007 | Curcio et al. |
| 2006/0193888 A1 | 8/2006 | Lye et al. | | 2007/0156231 A1 | 7/2007 | Weber |
| 2006/0193889 A1 | 8/2006 | Spradlin et al. | | 2007/0156248 A1 | 7/2007 | Marco et al. |
| 2006/0193890 A1 | 8/2006 | Owens et al. | | 2007/0160641 A1 | 7/2007 | Jang |
| 2006/0193892 A1 | 8/2006 | Furst et al. | | 2007/0168016 A1 | 7/2007 | Gronemeyer et al. |
| 2006/0195142 A1 | 8/2006 | Shalaby | | 2007/0173923 A1 | 7/2007 | Savage et al. |
| 2006/0198869 A1 | 9/2006 | Furst et al. | | 2007/0178129 A1 | 8/2007 | Flanagan |
| 2006/0199876 A1 | 9/2006 | Troczynski et al. | | 2007/0181433 A1 | 8/2007 | Birdsall et al. |
| 2006/0200229 A1 | 9/2006 | Burgermeister et al. | | 2007/0184083 A1 | 8/2007 | Coughlin |
| 2006/0200231 A1 | 9/2006 | O'Brien et al. | | 2007/0190104 A1 | 8/2007 | Kamath et al. |
| 2006/0200232 A1 | 9/2006 | Phaneuf et al. | | 2007/0191923 A1 | 8/2007 | Weber et al. |
| 2006/0200233 A1 | 9/2006 | Kujawski | | 2007/0191928 A1 | 8/2007 | Rolando et al. |
| 2006/0204441 A1 | 9/2006 | Atala et al. | | 2007/0191931 A1 | 8/2007 | Weber et al. |
| 2006/0204445 A1 | 9/2006 | Atala et al. | | 2007/0191943 A1 | 8/2007 | Shrivastava et al. |
| 2006/0210595 A1 | 9/2006 | Singhvi et al. | | 2007/0197980 A1 | 8/2007 | Barry et al. |
| 2006/0212108 A1 | 9/2006 | Tittelbach | | 2007/0202466 A1 | 8/2007 | Schwarz et al. |
| 2006/0222679 A1 | 10/2006 | Shanley et al. | | 2007/0207186 A1 | 9/2007 | Scanlon et al. |
| 2006/0222844 A1 | 10/2006 | Stinson | | 2007/0208412 A1 | 9/2007 | Elmaleh |
| 2006/0224237 A1 | 10/2006 | Furst et al. | | 2007/0219626 A1* | 9/2007 | Rolando et al. ............ 623/1.16 |
| 2006/0229711 A1* | 10/2006 | Yan et al. ............ 623/1.38 | | 2007/0224116 A1 | 9/2007 | Chandrasekaran et al. |
| 2006/0229713 A1 | 10/2006 | Shanley et al. | | 2007/0224244 A1 | 9/2007 | Weber et al. |
| 2006/0230476 A1 | 10/2006 | Atanasoska et al. | | 2007/0225799 A1 | 9/2007 | Doty |
| 2006/0233941 A1 | 10/2006 | Olson | | 2007/0244541 A1 | 10/2007 | Schulman |
| 2006/0241739 A1 | 10/2006 | Besselink et al. | | 2007/0244569 A1 | 10/2007 | Weber et al. |
| 2006/0251701 A1 | 11/2006 | Lynn et al. | | 2007/0250155 A1 | 10/2007 | Simpson |
| 2006/0259133 A1 | 11/2006 | Sowinski et al. | | 2007/0250156 A1 | 10/2007 | Palmaz |
| 2006/0264138 A1 | 11/2006 | Sowinski et al. | | 2007/0250158 A1 | 10/2007 | Krivoruchko et al. |
| 2006/0271156 A1 | 11/2006 | Ledergerber | | 2007/0255388 A1 | 11/2007 | Rudakov et al. |
| 2006/0271168 A1 | 11/2006 | Kleine et al. | | 2007/0255392 A1 | 11/2007 | Johnson |
| 2006/0271169 A1 | 11/2006 | Lye et al. | | 2007/0264199 A1 | 11/2007 | Labhasetwar et al. |
| 2006/0271192 A1 | 11/2006 | Olsen et al. | | 2007/0264303 A1 | 11/2007 | Atanasoska et al. |
| 2006/0275554 A1 | 12/2006 | Zhao et al. | | 2007/0270940 A1 | 11/2007 | Doty |
| 2006/0276877 A1 | 12/2006 | Owens et al. | | 2007/0270942 A1 | 11/2007 | Thomas |
| 2006/0276878 A1 | 12/2006 | Owens et al. | | 2007/0281073 A1 | 12/2007 | Gale et al. |
| 2006/0276879 A1 | 12/2006 | Lye et al. | | 2007/0281117 A1 | 12/2007 | Kaplan et al. |
| 2006/0276884 A1 | 12/2006 | Lye et al. | | 2007/0282432 A1 | 12/2007 | Stinson et al. |
| 2006/0276885 A1 | 12/2006 | Lye et al. | | 2007/0299509 A1 | 12/2007 | Ding |
| 2006/0280770 A1 | 12/2006 | Hossainy et al. | | 2007/0299512 A1 | 12/2007 | Korzuschnik et al. |
| 2006/0287709 A1* | 12/2006 | Rao ............ 623/1.15 | | 2008/0003251 A1 | 1/2008 | Zhou |
| 2006/0292388 A1 | 12/2006 | Palumbo et al. | | 2008/0003256 A1 | 1/2008 | Martens et al. |
| 2007/0003589 A1 | 1/2007 | Astafieva et al. | | 2008/0003431 A1 | 1/2008 | Fellinger et al. |
| 2007/0003596 A1 | 1/2007 | Tittelbach et al. | | 2008/0004691 A1 | 1/2008 | Weber et al. |
| 2007/0020306 A1 | 1/2007 | Schultheiss | | 2008/0031765 A1 | 2/2008 | Gerold et al. |
| 2007/0027532 A1 | 2/2007 | Wang et al. | | 2008/0033522 A1 | 2/2008 | Grewe et al. |
| 2007/0032858 A1 | 2/2007 | Santos et al. | | 2008/0033530 A1 | 2/2008 | Zberg et al. |
| 2007/0032862 A1 | 2/2007 | Weber et al. | | 2008/0033531 A1 | 2/2008 | Barthel et al. |
| 2007/0032864 A1 | 2/2007 | Furst et al. | | 2008/0033533 A1 | 2/2008 | Borck |
| 2007/0034615 A1 | 2/2007 | Kleine | | 2008/0033536 A1 | 2/2008 | Wittchow |
| 2007/0036905 A1 | 2/2007 | Kramer | | 2008/0033537 A1 | 2/2008 | Tittelbach |
| 2007/0038176 A1 | 2/2007 | Weber et al. | | 2008/0033538 A1 | 2/2008 | Borck et al. |
| 2007/0038289 A1 | 2/2007 | Nishide et al. | | 2008/0033539 A1 | 2/2008 | Sternberg et al. |
| 2007/0038290 A1 | 2/2007 | Huang et al. | | 2008/0033576 A1 | 2/2008 | Gerold et al. |
| 2007/0045252 A1 | 3/2007 | Kleine et al. | | 2008/0038146 A1 | 2/2008 | Wachter et al. |
| 2007/0048350 A1 | 3/2007 | Faltico et al. | | 2008/0050413 A1 | 2/2008 | Horvers et al. |
| 2007/0050007 A1 | 3/2007 | Kondyurin et al. | | 2008/0051335 A1 | 2/2008 | Kleiner et al. |
| 2007/0050009 A1 | 3/2007 | Flanagan | | 2008/0051866 A1 | 2/2008 | Chen et al. |
| 2007/0052497 A1 | 3/2007 | Tada | | 2008/0051872 A1 | 2/2008 | Borck |
| 2007/0055349 A1 | 3/2007 | Santos et al. | | 2008/0051881 A1 | 2/2008 | Feng et al. |
| 2007/0055354 A1 | 3/2007 | Santos et al. | | 2008/0057105 A1 | 3/2008 | Atanasoska et al. |
| 2007/0055364 A1 | 3/2007 | Hossainy et al. | | 2008/0058919 A1 | 3/2008 | Kramer-Brown et al. |
| 2007/0059435 A1 | 3/2007 | Santos et al. | | 2008/0058921 A1 | 3/2008 | Lindquist |
| 2007/0065418 A1 | 3/2007 | Vallana et al. | | 2008/0058923 A1 | 3/2008 | Bertsch et al. |
| 2007/0073385 A1 | 3/2007 | Schaeffer et al. | | 2008/0069854 A1 | 3/2008 | Xiao et al. |
| 2007/0073390 A1 | 3/2007 | Lee | | 2008/0069858 A1 | 3/2008 | Weber |
| 2007/0077163 A1 | 4/2007 | Furst et al. | | 2008/0071348 A1 | 3/2008 | Boismier et al. |
| 2007/0100385 A1 | 5/2007 | Rawat et al. | | 2008/0071349 A1 | 3/2008 | Atanasoska et al. |
| 2007/0104753 A1 | 5/2007 | Flanagan | | 2008/0071350 A1 | 3/2008 | Stinson |
| 2007/0106347 A1 | 5/2007 | Lin | | 2008/0071351 A1 | 3/2008 | Flanagan et al. |
| 2007/0106363 A1 | 5/2007 | Weber | | 2008/0071352 A1 | 3/2008 | Weber et al. |
| 2007/0123131 A1 | 5/2007 | Nguyen et al. | | 2008/0071353 A1 | 3/2008 | Weber et al. |
| 2007/0123973 A1 | 5/2007 | Roth et al. | | 2008/0071355 A1 | 3/2008 | Weber et al. |
| 2007/0129789 A1 | 6/2007 | Cottone, Jr. et al. | | 2008/0071357 A1 | 3/2008 | Girton et al. |
| 2007/0129792 A1 | 6/2007 | Picart et al. | | 2008/0071358 A1 | 3/2008 | Weber et al. |

| | | |
|---|---|---|
| 2008/0082162 A1 | 4/2008 | Boismier et al. |
| 2008/0086199 A1 | 4/2008 | Dave et al. |
| 2008/0086201 A1 | 4/2008 | Weber et al. |
| 2008/0090097 A1 | 4/2008 | Shaw et al. |
| 2008/0097577 A1 | 4/2008 | Atanasoska et al. |
| 2008/0103589 A1 | 5/2008 | Cheng et al. |
| 2008/0103594 A1 | 5/2008 | Loffler et al. |
| 2008/0107890 A1 | 5/2008 | Bureau et al. |
| 2008/0109072 A1 | 5/2008 | Girton |
| 2008/0113083 A1 | 5/2008 | Sutermeister et al. |
| 2008/0124373 A1 | 5/2008 | Xiao et al. |
| 2008/0131479 A1 | 6/2008 | Weber et al. |
| 2008/0140172 A1 | 6/2008 | Carpenter et al. |
| 2008/0140186 A1 | 6/2008 | Grignani et al. |
| 2008/0145400 A1 | 6/2008 | Weber et al. |
| 2008/0147175 A1 | 6/2008 | Krivoruchko et al. |
| 2008/0147177 A1 | 6/2008 | Scheuermann et al. |
| 2008/0148002 A1 | 6/2008 | Fleming |
| 2008/0152929 A1 | 6/2008 | Zhao |
| 2008/0160166 A1 | 7/2008 | Rypacek et al. |
| 2008/0160259 A1 | 7/2008 | Nielson et al. |
| 2008/0161906 A1 | 7/2008 | Atanasoska et al. |
| 2008/0171929 A1 | 7/2008 | Katims |
| 2008/0175885 A1 | 7/2008 | Asgari |
| 2008/0177378 A1 | 7/2008 | Asgari |
| 2008/0183269 A2 | 7/2008 | Kaplan et al. |
| 2008/0183277 A1 | 7/2008 | Atanasoska et al. |
| 2008/0183278 A1 | 7/2008 | Atanasoska et al. |
| 2008/0188927 A1 | 8/2008 | Rohde et al. |
| 2008/0195170 A1 | 8/2008 | Asgari |
| 2008/0195189 A1 | 8/2008 | Asgari |
| 2008/0195198 A1 | 8/2008 | Asgari |
| 2008/0208308 A1 | 8/2008 | Allen et al. |
| 2008/0208313 A1 | 8/2008 | Yu et al. |
| 2008/0208352 A1 | 8/2008 | Krivoruchko et al. |
| 2008/0213377 A1 | 9/2008 | Bhatia et al. |
| 2008/0215129 A1 | 9/2008 | Venturelli et al. |
| 2008/0215139 A1 | 9/2008 | McMorrow et al. |
| 2008/0215140 A1 | 9/2008 | Borck et al. |
| 2008/0241218 A1 | 10/2008 | McMorrow et al. |
| 2008/0243113 A1 | 10/2008 | Shastri et al. |
| 2008/0243230 A1 | 10/2008 | Lootz et al. |
| 2008/0243231 A1 | 10/2008 | Flanagan et al. |
| 2008/0243234 A1 | 10/2008 | Wilcox |
| 2008/0243240 A1 | 10/2008 | Doty et al. |
| 2008/0243242 A1 | 10/2008 | Kappelt et al. |
| 2008/0249600 A1 | 10/2008 | Atanasoska et al. |
| 2008/0249615 A1 | 10/2008 | Weber |
| 2008/0255508 A1 | 10/2008 | Wang |
| 2008/0255509 A1 | 10/2008 | Wang |
| 2008/0262589 A1 | 10/2008 | Nagura |
| 2008/0268308 A1 | 10/2008 | Schilling et al. |
| 2008/0269872 A1 | 10/2008 | Lootz et al. |
| 2008/0288048 A1 | 11/2008 | Rolando et al. |
| 2008/0290467 A1 | 11/2008 | Shue et al. |
| 2008/0294236 A1 | 11/2008 | Anand et al. |
| 2008/0294246 A1 | 11/2008 | Scheuermann et al. |
| 2008/0306584 A1 | 12/2008 | Kramer-Brown |
| 2009/0005862 A1 | 1/2009 | Nakatani et al. |
| 2009/0012599 A1 | 1/2009 | Broome et al. |
| 2009/0018639 A1 | 1/2009 | Kuehling |
| 2009/0018647 A1 | 1/2009 | Benco et al. |
| 2009/0018648 A1 | 1/2009 | Wittchow |
| 2009/0022771 A1 | 1/2009 | Lynn et al. |
| 2009/0024199 A1 | 1/2009 | Birdsall et al. |
| 2009/0024209 A1 | 1/2009 | Ozdil et al. |
| 2009/0024210 A1 | 1/2009 | Klocke et al. |
| 2009/0024211 A1 | 1/2009 | Wittchow |
| 2009/0028785 A1 | 1/2009 | Clarke |
| 2009/0030494 A1 | 1/2009 | Stefanadis et al. |
| 2009/0030500 A1 | 1/2009 | Weber et al. |
| 2009/0030504 A1 | 1/2009 | Weber et al. |
| 2009/0030506 A1 | 1/2009 | Klocke et al. |
| 2009/0030507 A1 | 1/2009 | Klocke et al. |
| 2009/0035351 A1 | 2/2009 | Berglund et al. |
| 2009/0043330 A1 | 2/2009 | To |
| 2009/0043374 A1 | 2/2009 | Nakano |
| 2009/0043380 A1 | 2/2009 | Blaha et al. |
| 2009/0048660 A1 | 2/2009 | Adden |
| 2009/0062905 A1 | 3/2009 | Moore, Jr. et al. |
| 2009/0069884 A1 | 3/2009 | Mueller |
| 2009/0076588 A1 | 3/2009 | Weber |
| 2009/0076596 A1 | 3/2009 | Adden et al. |
| 2009/0081293 A1 | 3/2009 | Murase et al. |
| 2009/0081450 A1 | 3/2009 | Ascher et al. |
| 2009/0088831 A1 | 4/2009 | Goto |
| 2009/0088834 A1 | 4/2009 | Wang |
| 2009/0093871 A1 | 4/2009 | Rea et al. |
| 2009/0095715 A1 | 4/2009 | Sabaria |
| 2009/0118809 A1 | 5/2009 | Scheuermann et al. |
| 2009/0118812 A1 | 5/2009 | Kokate et al. |
| 2009/0118813 A1 | 5/2009 | Scheuermann et al. |
| 2009/0118814 A1 | 5/2009 | Schoenle et al. |
| 2009/0118815 A1 | 5/2009 | Arcand et al. |
| 2009/0118818 A1 | 5/2009 | Foss et al. |
| 2009/0118819 A1 | 5/2009 | Merz et al. |
| 2009/0118820 A1 | 5/2009 | Gregorich et al. |
| 2009/0118821 A1 | 5/2009 | Scheuermann et al. |
| 2009/0118822 A1 | 5/2009 | Holman et al. |
| 2009/0118823 A1 | 5/2009 | Atanasoska et al. |
| 2009/0123517 A1 | 5/2009 | Flanagan et al. |
| 2009/0123521 A1 | 5/2009 | Weber et al. |
| 2009/0124956 A1 | 5/2009 | Swetlin et al. |
| 2009/0131540 A1 | 5/2009 | Hiromoto et al. |
| 2009/0143855 A1* | 6/2009 | Weber et al. ............. 623/1.42 |
| 2009/0149942 A1 | 6/2009 | Edelman et al. |
| 2009/0157165 A1 | 6/2009 | Miller et al. |
| 2009/0157172 A1 | 6/2009 | Kokate et al. |
| 2009/0164002 A1 | 6/2009 | Becher et al. |
| 2009/0171452 A1 | 7/2009 | Yamamoto et al. |
| 2009/0177273 A1 | 7/2009 | Piveteau et al. |
| 2009/0182290 A1 | 7/2009 | Harder et al. |
| 2009/0182337 A1 | 7/2009 | Stopek et al. |
| 2009/0182425 A1 | 7/2009 | Duda et al. |
| 2009/0192571 A1 | 7/2009 | Stett et al. |
| 2009/0192594 A1 | 7/2009 | Borck |
| 2009/0192595 A1 | 7/2009 | Nagura et al. |
| 2009/0192596 A1 | 7/2009 | Adden |
| 2009/0196899 A1 | 8/2009 | Birdsall et al. |
| 2009/0198320 A1 | 8/2009 | Mueller et al. |
| 2009/0202610 A1 | 8/2009 | Wilson |
| 2009/0204203 A1 | 8/2009 | Allen et al. |
| 2009/0208428 A1 | 8/2009 | Hill et al. |
| 2009/0208555 A1 | 8/2009 | Kuttler et al. |
| 2009/0214373 A1 | 8/2009 | Stinson et al. |
| 2009/0220612 A1 | 9/2009 | Perera |
| 2009/0228037 A1 | 9/2009 | Rego |
| 2009/0240323 A1 | 9/2009 | Wilcox |
| 2009/0254171 A1 | 10/2009 | Heikkila |
| 2009/0259300 A1 | 10/2009 | Dorogy, Jr. et al. |
| 2009/0270979 A1 | 10/2009 | Adden |
| 2009/0274737 A1 | 11/2009 | Borck |
| 2009/0281613 A1 | 11/2009 | Atanasoska et al. |
| 2009/0287301 A1 | 11/2009 | Weber |
| 2009/0287302 A1 | 11/2009 | Thomas et al. |
| 2009/0306584 A1 | 12/2009 | Schmidtlein et al. |
| 2009/0306756 A1 | 12/2009 | Cho et al. |
| 2009/0306765 A1 | 12/2009 | Weber |
| 2009/0306766 A1 | 12/2009 | Mcdermott et al. |
| 2009/0311300 A1 | 12/2009 | Wittchow |
| 2009/0312807 A1 | 12/2009 | Boudreault et al. |
| 2009/0319035 A1 | 12/2009 | Terry |
| 2009/0324684 A1 | 12/2009 | Atanasoska et al. |
| 2009/0326638 A1 | 12/2009 | Atanasoska et al. |
| 2010/0008970 A1 | 1/2010 | O'Brien et al. |
| 2010/0010621 A1 | 1/2010 | Klocke |
| 2010/0010640 A1 | 1/2010 | Gerold et al. |
| 2010/0015206 A1 | 1/2010 | Flanagan et al. |
| 2010/0016940 A1 | 1/2010 | Shokoohi et al. |
| 2010/0021523 A1 | 1/2010 | Scheuermann et al. |
| 2010/0023112 A1 | 1/2010 | Borck et al. |
| 2010/0023116 A1 | 1/2010 | Borck et al. |
| 2010/0028436 A1 | 2/2010 | Ohrlander et al. |
| 2010/0030326 A1 | 2/2010 | Radhakrishman et al. |
| 2010/0034899 A1 | 2/2010 | Harder et al. |
| 2010/0042205 A1 | 2/2010 | Atanasoska et al. |
| 2010/0042206 A1 | 2/2010 | Yadav et al. |
| 2010/0047312 A1 | 2/2010 | Wittchow |

| | | | | | | |
|---|---|---|---|---|---|---|
| 2010/0047324 A1 | 2/2010 | Fritz et al. | | WO | WO 99/47077 | 9/1999 |
| 2010/0049146 A1 | 2/2010 | Nielsen et al. | | WO | WO 99/64580 | 12/1999 |
| 2010/0049296 A1 | 2/2010 | Sarasam et al. | | WO | WO 00/25841 | 5/2000 |
| 2010/0049299 A1 | 2/2010 | Popowski et al. | | WO | WO 00/48660 | 8/2000 |
| 2010/0049300 A1 | 2/2010 | Harder | | WO | WO 00/51136 | 8/2000 |
| 2010/0055151 A1 | 3/2010 | Flanagan | | WO | WO 00/54704 | 9/2000 |
| 2010/0057188 A1 | 3/2010 | Weber | | WO | WO 00/66190 | 11/2000 |
| 2010/0057197 A1 | 3/2010 | Weber et al. | | WO | WO 01/49338 | 7/2001 |
| 2010/0070024 A1* | 3/2010 | Venturelli et al. ........... 623/1.22 | | WO | WO 01/78906 | 10/2001 |
| 2010/0075162 A1 | 3/2010 | Yang et al. | | WO | WO 01/80920 | 11/2001 |
| 2010/0076544 A1 | 3/2010 | Hoffmann et al. | | WO | WO 01/87371 | 11/2001 |
| 2010/0076556 A1 | 3/2010 | Tomantschger et al. | | WO | WO 02/45764 | 6/2002 |
| 2010/0081735 A1 | 4/2010 | Mao et al. | | WO | WO 02/47739 | 6/2002 |
| 2010/0082092 A1 | 4/2010 | Gerold | | WO | WO 02/053202 | 7/2002 |
| 2010/0087910 A1 | 4/2010 | Weber | | WO | WO 03/002243 | 1/2003 |
| 2010/0087911 A1 | 4/2010 | Mueller | | WO | WO 03/013396 | 2/2003 |
| 2010/0087914 A1 | 4/2010 | Bayer et al. | | WO | WO 03/035131 | 5/2003 |
| 2010/0087915 A1 | 4/2010 | Bayer et al. | | WO | WO 03/035134 | 5/2003 |
| 2010/0087916 A1 | 4/2010 | Bayer et al. | | WO | WO 03/035278 | 5/2003 |
| 2010/0092535 A1 | 4/2010 | Cook et al. | | WO | 03/046062 | 6/2003 |
| 2010/0106243 A1 | 4/2010 | Wittchow | | WO | WO 03/063733 | 8/2003 |
| 2010/0119576 A1 | 5/2010 | Harder et al. | | WO | WO 03/094990 | 11/2003 |
| 2010/0119581 A1 | 5/2010 | Gratz et al. | | WO | 2004/025332 | 3/2004 |
| 2010/0121432 A1 | 5/2010 | Klocke et al. | | WO | WO 2004/029313 | 4/2004 |
| 2010/0125325 A1 | 5/2010 | Allen et al. | | WO | WO 2004/043292 | 5/2004 |
| 2010/0125328 A1 | 5/2010 | Flanagan | | WO | WO 2004/093643 | 11/2004 |
| 2010/0131050 A1 | 5/2010 | Zhao | | WO | WO 2005/025449 | 3/2005 |
| 2010/0131052 A1 | 5/2010 | Kappelt et al. | | WO | WO 2005/065576 | 7/2005 |
| 2010/0161031 A1 | 6/2010 | Papirov et al. | | WO | WO 2005/079335 A2 * | 9/2005 |
| 2010/0217370 A1 | 8/2010 | Scheuermann et al. | | WO | WO 2005/110395 | 11/2005 |
| | | | | WO | WO 2005/118019 | 12/2005 |
| | FOREIGN PATENT DOCUMENTS | | | WO | WO 2006/008739 | 1/2006 |
| | | | | WO | WO 2006/060033 | 6/2006 |
| AU | 2003 203 722 | 11/2003 | | WO | WO 2006/060534 | 6/2006 |
| CA | 2 235 031 | 10/1998 | | WO | WO 2006/065356 | 6/2006 |
| CA | 2 346 857 | 5/2000 | | WO | WO 2006065665 A1 * | 6/2006 |
| CA | 2 371 800 | 8/2000 | | WO | WO 2006/077154 | 7/2006 |
| DE | 198 11 033 | 8/1999 | | WO | WO 2006/080381 | 8/2006 |
| DE | 198 56 983 | 12/1999 | | WO | WO 2006/097503 | 9/2006 |
| DE | 103 57 281 | 7/2005 | | WO | WO 2006/104644 | 10/2006 |
| DE | 103 61 941 | 7/2005 | | WO | WO 2006/108065 | 10/2006 |
| DE | 10 2006 38236 | 2/2008 | | WO | WO 2007/005806 | 1/2007 |
| EP | 0 006 544 | 6/1979 | | WO | WO 2007/013102 | 2/2007 |
| EP | 0 337 035 | 10/1989 | | WO | WO 2007/018931 | 2/2007 |
| EP | 0 615 769 | 9/1994 | | WO | WO 2007/024552 | 3/2007 |
| EP | 0 923 389 | 7/1998 | | WO | WO 2007/035791 | 3/2007 |
| EP | 0 923 912 | 6/1999 | | WO | WO 2007/079363 | 7/2007 |
| EP | 0 966 979 | 12/1999 | | WO | WO 2007/079636 | 7/2007 |
| EP | 0 972 563 | 1/2000 | | WO | WO 2007/082147 | 9/2007 |
| EP | 1 054 644 | 11/2000 | | WO | WO 2007/139668 | 12/2007 |
| EP | 1 071 490 | 1/2001 | | WO | 2008/034048 | 3/2008 |
| EP | 1 222 901 | 7/2002 | | WO | 2008/034066 | 3/2008 |
| EP | 1 260 214 | 11/2002 | | WO | 2008/036457 | 3/2008 |
| EP | 1 270 023 | 1/2003 | | WO | 2008/036548 | 3/2008 |
| EP | 1 273 314 | 1/2003 | | WO | 2008/036554 | 3/2008 |
| EP | 1 370 306 | 12/2003 | | WO | WO 2008/003450 | 3/2008 |
| EP | 1 389 471 | 2/2004 | | WO | 2008/062414 | 5/2008 |
| EP | 1 393 766 | 3/2004 | | WO | WO 2008/092436 | 8/2008 |
| EP | 1 419 793 | 5/2004 | | WO | WO 2008/106271 | 9/2008 |
| EP | 0 951 877 | 6/2004 | | WO | 2008/117315 | 10/2008 |
| EP | 0 875 218 | 2/2005 | | WO | WO 2008/118606 | 10/2008 |
| EP | 1 733 746 | 12/2006 | | WO | 2009/045773 | 4/2009 |
| EP | 1 752 167 | 2/2007 | | | | |
| EP | 1 465 552 | 5/2007 | | | OTHER PUBLICATIONS | |
| EP | 1 835 042 | 9/2007 | | | | |
| EP | 1 750 780 | 10/2007 | | | | |
| EP | 1 562 565 | 3/2008 | | | | |
| EP | 1 642 551 | 12/2008 | | | | |
| EP | 1 653 885 | 4/2009 | | | | |
| EP | 1 632 256 | 9/2009 | | | | |
| EP | 1 703 858 | 10/2009 | | | | |
| EP | 2 139 535 | 1/2010 | | | | |
| EP | 1 883 380 | 3/2010 | | | | |
| EP | 2 189 169 | 5/2010 | | | | |
| RU | 2 218 242 | 12/2003 | | | | |
| WO | WO 93/04118 | 3/1993 | | | | |
| WO | WO 97/11724 | 4/1997 | | | | |
| WO | WO 98/29025 | 7/1998 | | | | |
| WO | WO 98/48851 | 11/1998 | | | | |
| WO | WO 99/33410 | 7/1999 | | | | |

OTHER PUBLICATIONS

Wikipedia, the Free Encyclopedia. "Galvanic Corrosion". Downloaded from <http://en.wikipedia.org/wiki/Galvanic_corrosion>. on Mar. 11, 2011.*
U.S. Appl. No. 11/752,772, filed May 23, 2007.
U.S. Appl. No. 11/752,736, filed May 23, 2007.
U.S. Appl. No. 60/845,136, filed Sep. 15, 2006, Weber and Atanasoska.
U.S. Appl. No. 60/826,002, filed Sep. 18, 2006, Girton et al.
Eniola et al., "Characterization of Biodegradable Drug Delivery Vehicles with the Adhesive Properties of Leukocytes II: Effect of Degradation on Targeting Activity," *Biomaterials*, 26:661-670 (2005).
Huang et al., "A Review on Polymer Nanofibers by Electro-spinning and their Applications in Nanocomposites," 63:2223-2253 (2003).

Schetsky, L. McDonald, "Shape Memory Alloys," Encyclopedia of Chemical Technology (3rd ed.), John Wiley & Sons, 20:726-736 (1982).

Wang et al., "Characterisation of Severely Deformed Austenitic Stainless Steel Wire," *Materials Science and Technology*, 21(01):1323-1328 (2005).

Zhou et al., "Drug-loaded, Magnetic, hollow silica nanocomposites for nanomedicine," *Nanomedicine: Nanotechnology, Biology and Medicine*, 1:233-237 (2005).

US 6,533,715, 3/2003, Hossainy et al. (withdrawn).

U.S. Appl. No. 10/849,742, filed Mar. 20, 2004, Chen et al.

U.S. Appl. No. 60/845,136, filed Sep. 15, 2006, Weber et al.

"Galvanic cell" printout from wikipedia, 2 pgs, printed Oct. 28, 2005.

"Galvanic corrosion", http://www.corrosion-doctors.org/Aircraft/galvdefi.htm, 3 pgs., printed Oct. 28, 2005.

"Galvanic series" printout from Wikipedia, p. 1 of 2, printed Oct. 28, 2005.

"Best of the ACC Scientific Session 2002," *Rev. Cardiovasc. Med.*, 2002, 3(2):85-104.

"Corrosion Theory and Corrosion Protection," EM 1110-2-3400, 1995, 8 pages.

Aghion et al., "Newly Developed Magnesium Alloys for Powertrain Applications," *JOM*, 2003, p. 30.

Andión et al., "Corrosion behaviour at the interface of steel bars embedded in cement slurries. Effect of phenol polymer coatings," *Corrosion Science*, 2002, 44:2805-2816.

Antipov et al., "Polyelectrolyte Multilayer Capsule Permeability Control," *Colloids and Surfaces A: Physiochem. Eng. Aspects*, 2002, 198-200, 535-541.

Antipov et al., "Polyelectrolyte Multilayer Capsules as Vehicles with Tunable Permeability," *Advances in Colloid and Interface Science*, 2004, 111:49-61.

Arts et al., "Polyphenols and disease risk in epidemiologic studies," *Am. J. Clin. Nutr.*, 2005, 81:317S-325S.

Artyukhin et al., "Layer-by-Layer Electrostatic Self-Assembly of Polyelectrolyte Nanoshells on Individual Carbon Nanotube Templates," *Langmuir*, 2004, 20:1442-1448.

Bach et al., "Corrosion, Protection and Repassivation After the Deformation of Magnesium Alloys Coated With a Protective Magnesium Fluoride Layer," *JOM*, 2004, p. 343.

Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.

Baurschmidt et al., "The Electrochemical Aspects of the Thrombogenicity of a Material," *J. Bioengineering*, 1977, 1:261-278.

Berkland et al., "Controlling Surface Nano-structure Using Flow-Limited Field-Injection Electrostatic Spraying (FFESS) of poly(D,L-lactide-*co*-glycolide)," *Biomaterials*, 2004, 25:5649-5658.

Berry et al., "Functionalisation of magnetic nanoparticles for applications in biomedicine," *J. Phys. D: Appl. Phys.*, 2003, 36:R198-R206.

Bolz et al., "Effect of smooth, porous and fractal surface structure on the properties of an interface," *J. Materials Science: Materials in Medicine*, 1995, 6:844-848.

Brandau et al., "Nanoporous Ceramic Coatings for Synthesis of Radioactive Implants," *Journal of Nuclear Medicine Abstract Book*, Jun. 7, 2000, p. 244P, Abstract No. 1076.

Brückner et al., "Metal plasma immersion ion implantation and deposition (MPIIID): chromium on magnesium," *Surface and Coatings Technology*, 1998, 103-104, pp. 227-230.

Buescher et al., "Characterization of Wet-Chemically Nanostructured Stainless Steel Surfaces," *Mat. Res. Soc. Symp. Proc.*, 2001, 676:1-6.

Caruso et al., "Ultrathin Molybdenum Polyoxometalate-Polyelectrolyte Multilayer Films," *Langmuir*, 1998, 14:3462-3465.

Casan-Pastor et al., "Polyoxometalates: From Inorganic Chemistry to Materials Science," *Frontiers in Bioscience*, 2004, 9:1759-1770.

Chaieb et al., "Inhibition of the corrosion of steel in 1 M HCl by eugenol derivatives," *Applied Surface Science*, 2005, 246:199-206.

Changwen et al., "Polyoxometalate-based organic-inorganic hybrid materials"; http://www.solgel.com/articles/oct01/changwen.asp, Retrieved from the Internet on Nov. 1, 2004 (17 pages).

Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.

International Search Report/Written Opinion in PCT/US05/16600 mailed May 4, 2006, 15 pages.

International Preliminary Report on Patentability in PCT/US05/16600 mailed Nov. 30, 2006, 7 pages.

International Preliminary Report on Patentability in PCT/US07/78476 mailed Mar. 26, 2009, 7 pages.

Authorized Officer Simin Baharlou, International Search Report/Written Opinion in PCT/US07/66568 mailed Oct. 8, 2007, 11 pages.

Authorized Officer Simin Baharlou, International Preliminary Report on Patentability in PCT/US07/66568 mailed Oct. 23, 2008, 10 pages.

International Search Report/Written Opinion in PCT/US07/78505 mailed Mar. 4, 2008, 10 pages.

International Preliminary Report on Patentability in PCT/US07/78505 mailed Mar. 26, 2009, 7 pages.

Authorized Officer Athina Nickitas-Etienne, International Search Report/Written Opinion in PCT/US07/78449, mailed Jan. 13, 2009, 24 pages.

Authorized Officer Athina Nickitas-Etienne, International Preliminary Report on Patentability in PCT/US07/78449 mailed Mar. 26, 2009, 9 pages.

Authorized Officer Simin Baharlou, International Search Report/Written Opinion in PCT/US07/75072 mailed Jan. 25, 2008, 21 pages.

Authorized Officer Simin Baharlou, International Preliminary Report on Patentability in PCT/US07/75072 mailed Feb. 12, 2009, 9 pages.

International Search Report/Written Opinion in PCT/US07/78429 mailed Mar. 28, 2008, 13 pages.

International Preliminary Report on Patentability in PCT/US07/78429 mailed Apr. 2, 2009, 8 pages.

International Search Report/Written Opinion in PCT/US07/78411 mailed Mar. 6, 2008, 12 pages.

International Preliminary Report on Patentability in PCT/US07/78411 mailed Feb. 4, 2009, 8 pages.

Authorized Officer Elisabeth Reinecke, International Search Report/Written Opinion in PCT/US07/60137 mailed Jul. 27, 2007, 20 pages.

International Preliminary Report on Patentability in PCT/US07/78412 mailed Apr. 2, 2009, 7 pages.

Authorized Officer Trudy Hinterwimmer, International Search Report/Written Opinion in PCT/US07/78412 mailed Mar. 3, 2008, 10 pages.

Authorized Officer Joëlle Gerber, International Search Report/Written Opinion in PCT/US07/78450 mailed Nov. 19, 2008, 17 pages.

International Preliminary Report on Patentability in PCT/US07/78450 mailed Mar. 26, 2009, 7 pages.

International Search Report/Written Opinion in PCT/US07/73839 mailed Apr. 16, 2008, 17 pages.

International Preliminary Report on Patentability in PCT/US07/73839 mailed 2 Apr. 2, 2009, 10 pages.

Authorized Officer Cecilia Giel-Barragán Ramos, International Search Report/Written Opinion in PCT/US07/79841 mailed Feb. 4, 2009, 21 pages.

Authorized Officer Athina Nickitas-Etienne, International Preliminary Report on Patentability in PCT/US07/79841 mailed Apr. 30, 2009, 7 pages.

Authorized Officer Joëlle Gerber, International Search Report/Written Opinion in PCT/US07/88888 mailed Jul. 13, 2009, 24 pages.

Authorized Officer Nora Lindner, International Preliminary Report on Patentability in PCT/US07/88888 mailed Jul. 30, 2009, 11 pages.

Authorized Officer Véronique van Loon-Mégard, International Search Report/Written Opinion in PCT/US08/75976 mailed Nov. 25, 2008, 20 pages.

Authorized Officer Trudy Hinterwimmer, International Search Report/Written Opinion in PCT/US09/49422 mailed Aug. 24, 2009, 10 pages.

Damiani et al., "Vasorelaxant effects on eugenol on rat thoracic aorta," *Vascular Pharmacol.*, 2003, 40:59-66.

Dexter, "Galvanic Corrosion," MAS Note, University of Delaware Sea Grant Marine Advisory Service, 2003.

Di Mario et al., "MOONLIGHT: a controlled registry of an iridium-oxide coated stent with angiographic follow up," *Int. J. Cardiol.*, 2004, 95:329-331.

Dowling et al., "Anti-bacterial silver coatings exhibiting enhanced activity through the addition of Platinum," *Surf. & Coatings Tech.*, 2003, 163-164:637-640.

Duygu, "Controlled Release Systems," http://www.biomed.metu.edu.tr/courses/term_papers/contr-rel-sys_duygu.htm (Dec. 30, 2005).

Farhat et al., "Corrosion Control Using Polyelectrolyte Multilayers," *Electrochemical and Solid State Letters*, 2002, 5(4):B13-B15.

Ferrando, "Review of Corrosion and Corrosion Control of Magnesium Alloys and Composites," *J. Mater. Eng.*, 1989, 11:299-313.

Fischer et al., "Hydrogen in magnesium alloys and magnesium interfaces: preparation, electronic properties and interdiffusion," *J. Less Common Metals*, 1991, 172:808-815.

Fontenier et al., "Study of a 'Platinum-Magnesium' Cell to Supply Current to a Pacemaker," *Bioelectrochemistry and Bioenergetics*, 1975, 2(2):106-123.

Frei, "On the Role of Vitamin C and Other Antioxidants in Atherogenesis and Vascular Dysfunction," Proceedings—Society for Experimental Biology and Medicine, 1999, 222:196-204.

Gomes et al., "Alternative tissue engineering scaffolds based on starch: processing methodologies, morphology, degradation and mechanical properties," *Materials Science and Engineering C*, 2002, 20:19-26.

Grassi et al., "Short-term administration of dark chocolate is followed by a significant increase in insulin sensitivity and a decrease in blood pressure in healthy persons," *Am. J. Clin. Nutr.*, 2005, 81(3):611-614.

Gray and Luan, "Protective coatings on magnesium and its alloys—a critical review," *J. Alloys Compounds*, 2002, 336:88-113.*

Guo et al., "Multi-layer LB films of single-wall carbon nanotubes," *Physica B*, 2002, 323:235-236.*

Guo et al., "Manipulation of single-wall carbon nanotubes into aligned molecular layers," *Chem. Phys. Lett.*, 2002, 362:314-318.*

Gurib-Fakim, "Medicinal plants: Traditions of yesterday and drugs of tomorrow," *Molecular Aspects of Medicine*, 2006, 27:1-93.*

Haferkamp et al., "Magnesium-Base-Alloys as Implant-Material Steps to the Production of Thin Components," *Magnesium*, 2000, 159-164.*

Hau et al., "Surface-Chemistry Technology for Microfluidics," *J. Micromech. Microeng.*, 2003, 13:272-278.*

Heublein et al., "Biocorrosion of magnesium alloys: a new principle in cardiovascular implant technology?" *Heart*, 2003, 89:651-656.*

Heublein et al., "Bio-corrosion—a new principle for temporary cardiovascular implants?" *European Heart Journal, Journal of the European Society of Cardiology*, 2000, vol. 21, p. 286, Abstract No. P1605.*

Heublein et al., "Degradation of Metallic Alloys—A New Principle in Stent Technology?" *The American Journal of Cardiology*, Eleventh Annual Symposium Transcatheter Cardiovascular Therapeutics Abstracts, Sep. 22, 1999.*

Heublein et al., "Local Tissue Engineering by Biocorrosion Vision or Reality?" *The American Journal of Cardiology*, TCT Abstracts/Poster, Oct. 16, 2000.*

Ito et al., "Antioxidant action of eugenol compounds; role of metal ion in the inhibition of lipid peroxidation," *Food Chem. Toxicol.*, 2005, 43:461-466.*

Ivanova and Ivanov, "Mechanisms of the extracellular antioxidant defend," *Experimental Pathology and Parasitology*, 2000, 4:49-59.*

Jiang, "A review of wet impregnation—An alternative method for the fabrication of high performance and nano-structured electrodes of solid oxide fuel cells," *Materials Science and Engineering A*, 2006, 418:199-210.*

Kean and Davies, "Cathodic Protection," 7 pages, 1981; http://www.npl.co.uk/upload/pdf/cathodic_protection.pdf.*

Kim et al., "Comprehensive study on vitamin C equivalent antioxidant capacity (VCEAC) of various polyphenols in scavenging a free radical and its structural relationship," *Crit. Rev. Food Sci. Nutr.*, 2004, 44(4):253-273.*

Kim et al., "Effect of Anti-Oxidant (Carvedilol and Probucol) Loaded Stents in a Porcine Coronary Restenosis Model," *Circ. J.*, 2005, 69:101-106.*

Kong et al., "Polyelectrolyte-functionalized multiwalled carbon nanotubes: preparation, characterization and layer-by-layer self assembly," Polymer, 2005, 46:2472-2485.*

Kumar et al., "Polyanhydrides: an overview," *Advanced Drug Delivery Reviews*, 2002, 54:889-910.*

Kurth et al., "Multilayer on Solid Planar Substrates: From Structure to Function", *Multi-layer Thin Films Sequential Assembly of Nanocomposite Materials*, 2003, Chapter 14, pp. 393-426.*

Kurth et al., "Ultrathin Composite Films Incorporating the Nanoporous Isopolyoxomolybdate 'Keplerate' $(NH_4)_{42}[Mo_{132}O_{372}(CH_3COO)_{30}(H_2O)_{72}]$," *Chem. Mater.*, 2000, 12:2829-2831.*

Kutsenko et al., "Structural Changes in Mg Alloy induced by plasma immersion ion implantation of Ag," *Acta Materialia*, 2004, 52:4329-4335.*

Lambert et al., "Inhibition of carcinogenesis by polyphenols: evidence from laboratory investigations," *Am. J. Clin. Nutr.*, 2005, 81:284S-291S.*

Lee et al., "Retentive and compressive strengths of modified zinc oxide-eugenol cements," *J. Dentistry*, 2000, 28:69-75.*

Liao et al., "Fabrication of porous biodegradable polymer scaffolds using a solvent merging/particulate leaching method," *J. Biomed. Mater. Res.*, 2002, 59(4):676-681.

Lin et al., "Micropatterning proteins and cells on polylactic acid and poly(lactide-*co*-glycolide)," *Biomaterials*, 2005, 26:3655-3662.

Liu et al., "Sol-gel deposited TiO2 film on NiTi surgical alloy for biocompatibility improvement," *Thin Solid Films*, 2003, 429:225-230.

Liu, *Introduction to Corrosion and Protection*, Corrosion and Protection Centre, School of Materials, The University of Manchester, 2006, 36 pages.

Liu et al., "Layer-By-Layer Ionic Self-Assembly of Au Colloids Into Multilayer Thin-Films with Bulk Metal Conductivity," *Chemical Physics Letters*, 1998, 298:315-319.

Liu et al., "Functional Polyoxometalate Thin Films via Electrostatic Layer-by-Layer Self-Assembly," *Journal of Cluster Science*, 2003, 14:405-419.

Maier et al., "High concentrations of magnesium modulate vascular endothelial cell behaviour in vitro," *Biochim. Biophys. Acta*, 2004, 1689:6-12.

Mamedov et al., "Molecular Design of Strong Single-Wall Carbon Nanotube/Polyelectrolyte Multilayer Composites," *Nature Materials*, 2002, 1:190-194.

Matsuoka et al., "Hyperthermia Using Magnetite Cationic Liposomes for Hamster Osteosarcoma," *BioMagnetic Research and Technology*, 2004, 2:3-8.

Medical Device Daily, "Conor Cites Positive 12-month Results for Its CoStar Stent", May 2005 (1 page).

Middleton and Tipton, "Synthetic Biodegradable Polymers as Medical Devices," http://www.devicelink.com/mpb/archive/98/03/002.html, Mar. 1998, 9 pages.

Mihailovic et al., "Unusual Magnetic State in Lithium-Doped $MoS_2$ Nanotubes," *Phys. Rev. Lett.*, 2003, 90146401-1-4.

Mikos and Temenoff, "Formation of highly porous biodegradable scaffolds for tissue engineering," *Electronic Journal of Biotechnology*, 2000, 3(2):1-6.

Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.

Mohanty et al. "Evaluation of soft tissue response to a poly[urethane urea]," *Biomaterials*, 1992, 13(10):651-656.

Molnar and Garai, "Plant-derived anti-inflammatory compounds affect MIF tautomerase activity," *International Immunopharmacology*, 2005, 5:849-856.

Moskaug et al., "Polyphenols and glutathione synthesis regulation," *Am. J. Clin. Nutr.*, 2005, 81:277S-283S.

Naderi et al., "Effect of some volatile oils on the affinity of intact and oxidized low-density lipoproteins for adrenal cell surface receptors," *Mol. Cell. Biochem.*, 2004, 267:59-66.

Niemeyer et al., "Magnesium alloys as biodegradable metallic implant materials for cardiovascularic and orthopaedic surgery," *Euromat 2001, 7th European Conference on Advanced Materials and Processes*, Jun. 10-14, 2001 (Abstract).

Nilsson et al., "Development of a dosage method for electrochemical treatment of tumours: a simplified mathematical model," *Bioelectrochemistry and Bioenergetics*, 1998, 47:11-18.

Ou et al., "Protective effects of eugenol against oxidized LDL-induced cytotoxicity and adhesion molecule expression in endothelial cells," *Food Chem. Toxicol.*, 2004, 44:1485-1495.

Park et al., "Microstructural change and precipitation hardening in melt-spun Mg-X-Ca alloys," *Science and Technology of Advanced Materials*, 2001, 2:73-78.

Peuster et al., "Long-term biocompatibility of a corrodible peripheral iron stent in the porcine of descending aorta," *Biomaterials*, 2006, 27:4955-4962.

Prasse et al., "Electric Anisotropy of Carbon Nanofibre/Epoxy Resin Composites Due to Electric Field Induced Alignment," *Composites Science and Technology*, 2003, 63:1835-1841.

Ratnam et al., "Role of antioxidants in prophylaxis and therapy: A pharmaceutical perspective," *J. Controlled Release*, 2006, 113:189-207.

Remskar et al., "Self-Assembly of Subnanometer-Diameter Single-Wall $MoS_2$ Nanotubes," *Science*, 2001, 292:479-481.

Rezwan et al., "Biodegradable and bio active porous polymer/inorganic composite scaffolds for bone tissue engineering," *Biomaterials*, 2006, 27:3413-3431.

Rhule et al., "Polyoxometalates in Medicine," *Chem. Rev.*, 1998, 98:327-357.

Rutledge et al., "Electrostatic Spinning and Properties of Ultrafine Fibers," *National Textile Center Annual Report*, Nov. 2001, M01-D22, pp. 1-10.

Ryan et al., "Fabrication methods of porous metals for use in orthopaedic applications," *Biomaterials*, 2006, 27:2651-2670.

Sastry et al., "DNA-Mediated Electrostatic Assembly of Gold Nanoparticles into Linear Arrays by a Simple Drop-Coating Procedure," *Appl. Phys. Lett.*, 2001, 78:2943-2945.

Satoh et al., "Effect of Antioxidants on Radical Intensity and Cytotoxic Activity of Eugenol," *Anticancer Res.*, 1998, 18:1549-1552.

Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.

Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.

Sawyer et al., "Electrochemical Criteria in the Choice of Materials used in Vascular Prostheses," *Biophysical Mechanisms in Vascular Homeostasis and Intravascular Thrombosis*, 1965, pp. 337-348.

Shaw, "Corrosion Resistance of Magnesium Alloys," *ASM Handbook* vol. 13A: *Corrosion: Fundamentals, Testing, and Protection*, 2003, 5 pages.

Shenoy et al., "Role of Chain Entanglements on Fiber Formation During Electrospinning of Polymer Solutions: Good Solvent, Non-Specific Polymer-polymer Interaction Limit," *Polymer*, 2005, 46:3372-3384.

Shi et al., "A novel electrically conductive and biodegradable composite made of polypyrrole nanoparticles and polylactide," *Biomaterials*, 2004, 25:2477-2488.

Shin, "Experimental Characterization of Electrospinning: the Electrically Forced Jet and Instabilities," *Polymer*, 2001, 42:9955-9967.

Singh et al., "Electrocatalytic Activity of Electrodeposited Composite Films of Polypyrrole and $CoFe_2O_4$ Nanoparticles Towards Oxygen Reduction Reaction," *Electrochimica Acta*, 2004, 49:4605-4612.

Song et al., "Galvanic corrosion of magnesium alloy AZ91D in contact with an aluminium alloy, steel and zinc," *Corrosion Science*, 2004, 46:955-977.

Stoclet et al., "Vascular protection by dietary polyphenols," *Eur. J. Pharmacol.*, 2004, 500:299-313.

Straumal et al., "Vacuum arc deposition of protective layers on glass and polymer," *Thin Solid Films*, 2001, 383:224-226.

Suhaj, "Spice antioxidants isolation and their antiradical activity: a review," *J. Food Composition and Analysis*, 2006, 19:531-537.

Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.

Suslick et al., "The Photochemistry of Chromium, Manganese, and Iron Porphyrin Complexes," *J. Chem.*, 1992, 16:633-642.

Tada et al., "Distribution of pH during galvanic corrosion of a Zn/steel couple," *Electrochimica Acta*, 2004, 49:1019-1026.

Tan et al., "Systematic Parameter Study for Ultra-Fine Fiber Fabrication Via Electrospinning Process," *Polymer*, 2005, 46:6128-6134.

Tian et al., "Corrosion resistance improvement of magnesium alloy using nitrogen plasma ion implantation," *Surface & Coatings Technology*, 2005, 198:454-458.

Vermette et al., "Immobilized Liposome Layers for Drug Delivery Applications," *J. Controlled Release*, 2002, 80:179-195.

von Euler et al., "Cell proliferation and apoptosis in rat mammary cancer after electrochemical treatment (EChT)," *Bioelectrochemistry*, 2004, 62:57-65.

Vrbanic et al., "Air-Stable Monodispersed $Mo_6S_3I_6$ Nanowires," *Nanotechnology*, 2004, 15:635-638.

Wallerath et al., "A blend of polyphenols explains the stimulatory effect of red wine on human endothelial NO synthase," *Nitric Oxide*, 2005, 12(2):97-104.

Wan et al., "Influence of Plasma Immersion Ion Implantation on Corrosion Properties of Magnesium," South Jiaotong University, Chengdu, 2005.

Wang et al., "Nonlinear optical properties of thin iron films grown on MgO (100) by pulsed laser deposition," *Thin Solid Films*, 2005, 471:86-90.

Wang, "Recent development of non-platinum catalysts for oxygen reduction reaction," *J. Power Sources*, 2005, 152:1-15.

Weber et al., "Hardness and corrosion resistance of single-phase nitride and carbide on ion," *Materials Science and Engineering*, 1995, 99:205-210.

Weh et al., "Evolution of afractal-like surface structures in layers of polyacrylonitrile solutions by interfacial dynamic processes," *J. Colloid and Interface Science*, 2004, 271:407-415.

Widmer et al., "Manufacture of porous biodegradable polymer conduits by an extrusion process for guided tissue regeneration," *Biomaterials*, 1998, 19:1945-1955.

Wieneke et al., "Stent Coating: A New Approach in Interventional Cardiology," *Herz*, 2002, 27(6):518-526.

Williamson et al., "Bioavailability and bioefficacy of polyphenols in humans. II. Review of 93 intervention studies," *Am. J. Clin. Nutr.*, 2005, 81:243S-255S.

Witte et al., "In vitro and in vivo corrosion measurements of magnesium alloys," *Biomaterials*, 2006, 27:1013-1018.

Yamaguchi et al., "Mg2Si Coating Technology on Magnesium Alloys to Improve Corrosion and Wear Resistance", *JOM*, 2004, p. 343.

Yi et al., "Characterization of a bioactive nanotextured surface created by controlled chemical oxidation of titanium," *Surface Science*, 2006, 600:4613-4621.

You et al., "The Effect of Calcium Additions on the Oxidation Behavior in Magnesium Alloys," *Scripta Mat.*, 2000, 42:1089-1094.

Yu and Uan, "Sacrificial Mg film anode for cathodic protection of die cast Mg-9-wt.%-1 wt.%Zn alloy in NaC1 aqueous solution," *Scripta Mat.*, 2006, 54:1253-1257.

Yue et al., "Improvement in the Corrosion Resistance of Magnesium ZK60/SiC Composite by Excimer Laser Surface Treatment," *Scripta Materialia*, 1998, 38(2):191-198.

Zeta Potential-An Introduction in 30 Minutes, Technical Note; http://www.nbtc.cornell.edu/facilities/downloads/Zeta%20potential%20-%20An%20introduction%20in%2030%20minutes.pdf, Retrieved from the Internet on May 9, 2005 (6 pages).

Zhang et al., "Natural Polyelectrolyte Films Based on Layer-by-Layer Deposition of Collagen and Hyaluronic Acid," *Biomaterials*, 2005, 26:3353-3361.

Zhang et al., "Improving multilayer films endurance by photoinduced interaction between Dawson-type polyoxometalate and diazo resin," *Materials Chemistry and Physics*, 2005, 90:57-52.

Zhang et al., "Ways for fabricating stable layer-by layer self-assemblies: combined ionic self-assembly and post chemical reaction," *Colloids and Surfaces A: physiochemical and Engineering Aspects*, 2002, pp. 198-200, 439-442.

Zucchi et al., "Influence of a silane treatment on the corrosion resistance of a WE43 magnesium alloy," *Surface Coatings Technol.*, 2006, 200:4136-4143.

Aaltonen, "Atomic Layer Deposition of Noble Metal Thin Films," *University of Helsinki*, Apr. 8, 2005, pp. 1-71.

Albion Research Notes, Newsletter, Oct. 1994, 3(4): 1-4.

Anand et al., "Ion-exchange resins: carrying drug delivery forward," *DDT*, 2001, 6: 905-914.

Anderson et al., "A new conductive polymer as a replacement for chrome conversion coatings," *2003 Aerospace Coatings Removel and Coatings Conference*,May 20-22, 2003, Colorado Springs, CO, 7 pages.

Ashtari et al. "An efficient method for recovery of target ssDNA based on amino-modified silica-coated magnetic nanoparticles" *Talanta 67*. (2005). 548-554.

Atta, "Electrochemical synthesis, characterization and some properties of a polymer derived from thioflavin S.," *European Polymer Journal*, 2005, 41: 3018-3025.

Australian Government, Department of Health and Aging, "Horizon Scanning Technology Prioritising Summary-Biodegradable stents for coronary artery disease," *Australia and New Zealand Horizon Scanning Network (ANZHSN)*, Aug. 2007, pp. 1-13.

Babapulle and Eisenberg, "Coatred stents for their prevention of restenosis: Part II," *Circulation*, 2021, 106: 2849-2866.

Balasubramanian et al. "Dispersion and Stability Studies of Resorcinarene-Encapsulated Gold Nanoparticles." *Langmuir*, 2002, 1676-3681.

Bao, Y. et al. "Preparation of functionalized and gold-coated cobalt nanocrystals for biomedical applications." *Journal of Magnetism and Magnetic Materials*, 2005, 293:15-19.

Bekesi et al., "Efficient Submircon Processing of Metals with Femto," *Appl. Phys. A.*, Published Oct. 25, 2002, pp. 355-357.

Ben-Hamu et al., "Influence of Si, Ca and Ag addition on corrosion behaviour of new wrought Mg-Zn alloys," *Materials Science and Technology*, 2006, vol. 22, No. 10, pp. 1213-1218.

Bereket et al., "Electrochemical synthesis and anti-corrosive properties of polyaniline, poly(2-anisidine), and poly(aniline-co-2-anisidine) films on stainless steel," *Progress in Organic Coatings*, 2005, 54: 63-72.

Bernkop-Schnurch, "Chitosan and its derivatives: potential excipients for peroral peptide delivery systems," *International J. of Pharmaceutics*, 2000, 194: 1-13.

Biercuk et al., "Low-temperature atomic-layer-deposition lift-off method for microelectronic and nanoelectronic applications," *Applied Physics Letters*, vol. 83, No. 12, Sep. 22, 2003, pp. 2405-2407.

Blanusa et al., "Chelators as Antidotes of Metal Toxicity Therapeutic and Experimental Aspects," *Current Medicinal Chemistry*, 2005, vol. 12, pp. 2771-2794.

Bosiers et al., "Absorbable Metal stent for CLI in Infrapopliteal lesions: 1 year results," *CX 2005 Global Endovascular Forum*, Apr. 2005, pp. 1-23.

Brunatto and Muzart, "Influence of the gas mixture flow on the processing parameters of hollow cathode discharge ion sintering," *J. Phys. D.: Appl. Phys.*, 2007, 40: 3937-3944.

Brunner et al., "Porosity Tailored Growth of Black Anodic Layers on Magnesium in an Organic Electrolyte," *Journal of the Electrochemical Society*, vol. 156 (2), Dec. 12, 2008, pp. C62-C66.

Chang et al., "Effect of Heat Treatment on Corrosion and Electrochemical behavior of Mg-3Nd-0.2Zn-0.4Zr (wt. %) alloy," *Science Direct, Electrochimica Acta 52*, 2007, 3160-3167.

Chang et al., "Templated sythesis of Gold-iron Alloy nanoparticles using pulsed laser deposition," *Nanotechnology*, vol. 17, 2006, pp. 5131-5135.

Chen et al., "Laser Cladding of Mg20A18o Powder on ZM5 Magnesium Alloy," *Corrosion Engineering, Science and Technology*, 2007, vol. 42, No. 2, pp. 130-136.

Cheng et al., "Electrogeneration and electrochemical properties of hybrid materials: polypyrrole doped with polyoxometalates $PW_{12-x}Mo_xO_{40}{}^{3-}(x=0,3,6,12)$," *Synthetic Metals*, 2002, 129: 53-59.

Cho et al., "Gold-coated iron nanoparticles: a novel magnetic resonance agent for $T_1$ and $T_2$ weighted imaging," *Nanotechnology*, vol. 17, 2006, pp. 640-644.

Chou et al., "Electrochemical treatment of mouse and rat fibrosarcomas with direct current," *Bioelectromagnetics*, 1997, 18:14-24.

Cogger et al. "An Introduction to Electrochemical Impedance Measurement," *Solartron Analytical*, 1999, 2-14.

Conolly et al., "X-Ray microtomography studies of localized corrosion and transitions to stress corrosion cracking," *Materials Science and Technology*, 2006, vol. 22, No. 9, pp. 1076-1085.

Costa et al., "The effect of the magnetic field on the corrosion behavior of Nd-Fe-B permanent magnets." *Journal of Magnetism and Magnetic Materials*, 278, 2004, pp. 348-358.

Damen et al., "Paclitaxel esters of malic acid as prodrugs with improved water solubility," *Bioorganic & Medicinal Chemistry*, 2000, 8: 427-432.

Davies, "Changing the salt, changing the drug," *The Pharmaceutical Journal*, 2001, 266: 322-323.

De Geest et al., "Self-rupturing Microcapsules," *Adv. Mater.*, 2005, vol. 17, pp. 2357-2361.

de Witte, "Analysis of the principal component of external casing corrosion in deep wells," *J. Appl. Electrochem.*, 1985, 15: 325-334.

Di Mario et al., "Drug-eluting bioabsorbable magnesium stent," *J. Interventional Cardiol.*, 2004, 17(6): 391-395.

Duncan et al., "Polymer-drug conjugates, PDEPY and PELT: basic principles for design and transfer from the laboratory to clinic," *Journal of Controlled Release*, 2001, 74: 135-146.

Duncan, "The dawning era of polymer therapeutics," *Nature Reviews/Drug Discovery*, 2003, 2: 347-360.

Eggebrecht et al., "Novel Magnetic Resonance-Compatible Coronary Stent: The Absorbable Magnesium-Alloy Stent," *Circulation*, 2005, 112: 303-304.

Erbel et al., "Absorbierbare Stents-Eine Vielversprechende Neuerung?" *Urban & Vogel*, No. 4, 2007, pp. 308-319.

Erbel et al., "Temporary scaffolding of coronary arteries with bioabsorbable magnesium stents: a prospective, non-randomised multicentre trial," *Lancet*, 2007, vol. 369, pp. 1869-1875.

Erne et al., "The Road to Bioabsorbable Stents: Reaching Clinical Reality?" *Cardio Vascular and Interventional Radiology*, Sep. 26, 2005, pp. 11-16.

International Preliminary report on Patentability in PCT/US2007/078417, mailed Mar. 26, 2009, 8 pages.

International Preliminary Report on Patentability, in PCT/US2007/078407, mailed Mar. 26, 2009, 6 pages.

European Search Report from EP 10159664.1, mailed Jun. 4, 2010, 3 pages.

Falotico, "Cordis Fully Bioabsorbable Stent Program," *Euro PCR09*, May 22, 2009, pp. 1-21.

Fan et al., "Influence of Lanthanum on the microstructure, mechanical property and corrosion resistance of magnesium alloy," *J. Mater Sci*, 2006, vol. 41, pp. 5409-5416.

Fan et al., "Metallic Stents Coated with Bioabsorable Polymers," *Cardiac Interventions Today*, Jun./Jul. 2009, pp. 42-49.

Feng et al., "Sonochemical preparation of photochromic nanocomposite thin film based on polyoxometalates well dispersed in polyacrylamide," *Journal of Solid State Chemistry*, 2002, 169: 1-5.

Feng et al., "Superplasticity and texture of SiC whiskers in a magnesium-based composite," *Scripta Materialia*, 2005, 53: 361-365.

Ferguson et al., "Corrosion—Fatigue Performance of Magnesium Alloys," *International Journal of Modern Physics B*, vol. 17, Nos. 8 & 9, 2003, pp. 1601-1607.

Fischer et al., "Determination of in-vivo corrosion rates of degradable implants by SR-microtomography," date unknown, pp. 1-2.

Franhofer Institut Fertigungstechnik Material forschung, Evaluation of metal injection moulding (MIM) and extrusion as processing technology for biodegradable stents (A 208143), 8 pages.

Franhofer Institut Fertigungstechnik Material forschung, "Phase 2: Evaluation of mictoextrusion," 4 pages.

Fraunhofer EZRT, "Quantitative material analysis by dual energy computed tomography for industrial NDT applications," 2009, 1 pg.
Fraunhofer IIS—Poster (German), "Prinzip der hochauflösenden Comptuertomographie," 2009, 1 page.
Gabrielli, Claude. "Use and Applications of Electrochemical Impedance Techniques," *Solartron Analytical*, 1997, 1-102.
Garner et al., "Polypyrrole-heparin composites as stimulus-responsive substrates for endothelial cell growth," *J. Biomed. Mater. Res.*, 1999, 44: 121-129.
Gettleman et al., "Measurement of in vivo corrosion rates in baboons, and correlation with in vitro tests," Journal of Dental Research, 1980, 59: 689-707.
Gettleman et al., "Materials Science: Measurement of in vivo Corrosion Rates in Baboons, and Correlation with in vitro Tests," *Journal of Dental Research*, 1980, vol. 59, pp. 689-707.
Griffiths et al., "Future devices: bioabsorbable stents," *Br. J. Cardiol.* (*Acute & Interventional Cardiology*), 2004, 11: AIC80-AIC84.
Grube, "Bioabsorbable Stents—The Boston Scientific & REVA Technology," *EuroPCR 2009*, 2009, pp. 1-27.
Gu et al., "In vitro Corrosion and biocompatibility of binary magnesium alloys," *Biomaterials*, vol. 30, 2009, pp. 484-498.
Gupta et al., "Nanometer spaced electrodes using selective area atomic layer deposition," *Applied Physics Letters*, vol. 90, 2007, pp. 1-4.
Haenzi et al., "Design strategy for microalloyed ultra-ductile Mg alloys," 2009, *Phil. Mag. Letters*, 89(6): 377-390.
Haenzi et al., "Design strategy for new biodegradable Mg-Y-Zn alloys for medical applications," *Int. J. Mat. Res.*, 2009, 100: 1127-1136.
Haenzi et al., "On the biodegradation performance of an Mg-Y-Re alloy with various surface conditions in simulated body fluid," *Acto Biomat.*, 2009, 5: 162-171.
Hamu et al., "Influence of Si, Ca and Ag addition on corrosion behavior of new wrought Mg-Zn alloys," 2006, 22(10): 1213-1218.
Hänzi et al., "Design strategy for microalloyed ultra-ductile magnesium alloys," *Philosophical Magazine letters*, vol. 89, No. 6, Jun. 2009, pp. 377-390.
Hänzi et al., "Design strategy for new biodegradable Mg-Y-Zn alloys for medical applications," *Int J. Mat. Res.*, vol. 100, 2009, pp. 1127-1136.
Hänzi et al., "On the biodegradation performance of an Mg-Y-Re alloy with various surface conditions in simulated body fluid," *Acta Biomaterialia*, vol. 5, 2009, pp. 162-171.
Haque et al. "Bioabsorption Qualities of Chitosan-absorbable Vascular Templates," *Current Surgery*, 2001, 58(1): 77-80.
Heismann et al., "Density and atomic number measurements with spectral x-ray attenuation method," *Journal of Applied Physics*, vol. 94, No. 3, Aug. 1, 2003, pp. 2073-2079.
Hermawan et al., "Developments in metallic biodegradable stents," *Acta Biomaterialia*, 2010, 6: 1693-1697.
Hermawan et al., "Degradable metallic biomaterials: Design and development of Fe-Mn alloys for stents," *Wiley InterScience: Article*, Apr. 19, 2008, pp. 1-12.
Hermawan et al., "Degradation Behaviour of Metallic Biomaterials for Degradable Stents," *Advanced Materials Research*, 2007, 15-17:113-118.
Hermawan et al., "Development of Degradable Fe-35Mn Alloy for Biomedical Application," *Advanced Material Research*, 2007, 15-17:107-112.
Hermawan et al., "Fe-Mn Alloys for Metallic Biodegradable Stents: Degradation and Cell Viability Studies," *Acta Biomaterialia*, Manuscript, Mar. 27, 2009, pp. 1-30.
Hermawan, et al., "Iron-Manganese: new class of metallic degradable biomaterials prepared by powder metallurgy," *Powder Metallurgy*, 2008, 51(1):38-45.
Hildebrandt et al., "Prevention of surface encrustation of urological implants by coating with inhibitors," *Biomaterials*, 2001, 22:503-507.
Holclajtner-Antunovic et al., "Study of some polyoxometallates of Keggin's type as potention antitumour agents," *Jugoslov Med. Biohem.*, 2004, 23: 25-30.
Hourng et al., Influence of multisteps thermal control in metal powder injection moulding process, *Powder Metallurgy*, 2008, 51: 84-89.

Hutten, A. et al. "Ferromagnetic FeCo nanoparticles for biotechnology". (2005) *Journal of Magnetism and Magnetic Materials* 293:93-101).
Iakovou et al., "Incidence, Predictors, and Outcome of Thrombosis Successful Implantation of Drug-Eluting Stents," *JAMA*, 2005, 293(17): 2126-2130.
Ignat et al., "Magnesium alloys (WE43 and ZE41) characterization for laser applications," *Applied Surface Science*, 2004, 233:382-391.
Iida et al. "Surface modification of of $\lambda Fe_2O_3$ nanoparticles with aminopropylsilyl groups and interparticle linkage with with $\alpha,\omega$-Dicarboxylic Acids". *Electrochimica Acta*. 2005. 855-859.
Imgrund, "Evaluation of metal injection moulding (MIM) and extrusion as processing technology for biodegradable stents. A 208143: Final report for phase I MIM of Fe and Fe-Si powders and sample characterisation," Aug. 15, 2008, *Fraunhofer Institut Fertigungstechnik Material forschung*, 18 pages.
Integran, "Biodegradable Nanometallic Intracoronary Stents," May 12, 2009, 1 page.
Integran, "Biodegradable Nanometallic Intracoronary Stents," Proposal, May 12, 2009, 1 page.
International Preliminary Report on Patentability from PCT/US09/043326 mailed Nov. 18, 2010, 7 pages.
International Preliminary Report on Patentability in PCT/US2007/078479, mailed Mar. 26, 2009, 8 pages.
International Search Report / Written Opinion in PCT/US09/046750 mailed Jul. 20, 2010, 14 pages.
International Search Report and Written Opinion from PCT/US09/043591, mailed Jun. 30, 2010, 10 pages.
International Search Report and Written Opinion in PCT/US2007/078417, mailed Jan. 22, 2009, 18 pages.
International Search Report and Written Opinion in PCT/US2007/078479, mailed Dec. 30, 2008, 12 pages.
International Search Report from PCT/US 03/20215, mailed Nov. 11, 2003, 4 pages.
International Search Report from PCT/US07/005671, mailed Jun. 2, 2008, 10 pages.
International Search Report/Written Opinion in PCT/US2007/078407, mailed Mar. 26, 2008, 10 pages.
International Search Report/Written Opinion in PCT/US2008/86639 mailed Feb. 23, 2010, 8 pages.
International Search Report/Written Opinion in PCT/US2009/43326 mailed Aug. 6, 2009, 9 pages.
Jabara et al., "Bioabsorbable Stents: The Future is Near," *Cardiac Interventions Today*, Jun./Jul. 2009, pp. 50-53.
Jabara, "Poly-anhydride based on salicylic acid and adipic acid anhydride," Glimpse into the future: bioabsorbable stents-aimint to restore vascular integrity, *Euro PCR09*, 2009, pp. 1-34.
James A. Plambeck, "Electrolytic Processes of Nonmetals," *Chemical Sciences*, 1995, 2 pages.
Jiang et al., "Corrosion protection of polypyrrole electrodeposited on AZ91 magnesium alloys in alkaline solutions," *Synthetic Materials*, 2003, 139: 335-339.
Jiang et al., "Effect of $TiB_2$ particulate on partial remelting behavior of Mg-11A1-0.5Zn matrix composite," *Materials Science and Engineering A*, 2004, 381: 223-229.
Kaesel et al., "Approach to Control the Corrosion of Magnesium by Alloying," *Magnesium: Proceedings of the 6th International Conference Magnesium Alloys and Their Applications*, 2004, pp. 534-539.
Kainer, "Magnesium alloys and technology," Wiley VCH, 2003, 119 pages.
Kaya et al., "Microstructure and Corrosion Resistance of Alloys of the Mg-Zn-Ag System," *Metal Science and Heat Treatment*, 2006, 48(11-12): 524-530.
Kececioglu, "Zur Biokompatibilitat eines neu entwickelten Stentmaterials aus korrodierbarem Reineisen," Jan. 25, 2007, pp. 1-131, *Ruhr-Universitat-Bochum*.
Kidambi et al., "Selective depositions on polyelectrolyte multilayers: self-assembled monolayers of m-dPEG acid as molecular template," *J. Am. Chem. Soc.*, 2004, 126: 4697-4703.
Kokubo et al., "How useful is SBF in predicting in vivo bone bioactivity?" *Biomaterials*, 2006, 27: 2907-2915.
LaFont, "Arterial Remodeling Technologies: Bioresorbable Stents," *Euro PCR09*, 2009, pp. 1-28.

Lee, J. et al. "Simple synthesis of mesoporous carbon with magnetic nano particles embedded in carbon rods". (2005) Carbon 43:2536-2543.

Lee, Sang-Yup et al. "Surface modification of magnetic nanoparticles capped by oleic acids: Characterization and colloidal stability in polar solvents" *Journal of Colloid and Interface Science* 293 (2006) 401-408.

Levesque et al., "Design of pseudo-physiological test bench specific to the development of biodegradable metallic biomaterials," *Acta Biomaterialia*, 2008, 4:284-295.

Li et al., "The corrosion inhibition of the self assembled Au, and Ag nonoparticles films on the surface of copper," Colloids and Surfaces A: Physiochem. Eng. Aspects, 2006, 273: 16-23.

Li et al., "Effects of Direct Current on Dog Liver: Possible Mechanisms for Tumor Electrochemical Treatment," *Bioelectromagnetics*, 1997, 18:2-7.

Li et al., "Photoacoustic Tomography and Sensing in Biomedicine," *Phys. Med. Biol.*, 2009, 54:59-97.

Li, "Poly(L-glutamic acid)-anticancer drug conjugates," *Advanced Drug Delivery Reviews*, 2002, 54: 695-713.

Liu et al., "Characterizations of polypyrrole (PPy) nano-tubules made by templated ac electropolymerization," *European Polymer Journal*, 2005, 41: 2117-2121.

Lu et al. "Magnetic Switch of Permeability for Polyelectrolyte Microcapsules Embedded with Co@Au Nanoparticles". *American Chemical Society*. 2004.

Lu et al., "Theoretical analysis of calcium phosphate precipitation in simulated body fluid," *Biomaterials*, 2005, 26:1097-1108.

Ma et al., "Inhibition effect of self-assembled films formed by gold nonoparticles on iron surface," *Applied Surface Science*, 2006, 252: 4327-4334.

Macias et al., "Electrospun mesoporous oxide fibers," *Microporous and Mesoporous Materials*, 2005, 86: 1-13.

Maendl, "Zerstaubungsabscheidung von Mg-Legierungen," *Leibniz-Institut fur Oberflachenmodifizierung*, 2001, pp. 1-17.

Maeng et al., "Negative Vascular Remodelling after Implantation of Bioabsorbable Magnesium Alloy Stents in Porcine Coronary Arteries: A randomized Comparison with Bare-Metal and Sirolimus-Eluting Stents," *Heart*, 2009, 95:241-246.

Mani et al., "Coronary Stents: A materials perspective," *Biomaterials*, 2007, 28:1689-1710.

Mansfeld, Florian. "Analysis and Interpretation of EIS Data for Metals and Alloys," *Solartron Analytical*, 1999, 1-77.

Marijan et al. "Surface Modification of Stainless Steel-304 Electrode. 2. An Experimental Comparative Study of Electrochemically, Hydrothermally and Chemically Modified Oxide Films." *CCACAA*, 1999, 72(4) 751-761.

Markman, "Absorbable Coronary stents," *The Lancet*, Jun. 2, 2007, 369:1839-1840.

Massaro et al., "Comparative Investigation of the surface properties of commercial titanium dental implants. Part 1: chemical composition," *Journal of Materials Science: Materials in Medicine*, vol. 13, 2002, pp. 535-548.

Meng Han, "Laser nitriding of metals: Influences of the ambient pressure and the pulse duration," 2001, Dissertation, Georg-August-Universität Göttingen, 134 pages.

*Methods in Cell Biology (Cell Death)*, vol. 46, p. 163.

Miao et al., "Porous Calcium Phosphate Ceramics prepared by coating polyurethane foams with Calcium phosphate cements," *Materials Letters*, vol. 58, 2004, pp. 397-402.

Mueller et al., "Control of smooth muscle cell proliferation by ferrous iron," *Biomaterials*, vol. 27, 2006, pp. 2193-2200.

Mueller et al., "Magnesium and its Alloys as Degradable Biomaterials, Corrosion Studies Using Potentiodynamic and EIS Electrochemical Tenchiques," *Materials Research*, 2007, 10(1): 5-10.

Mueller et al., "Preparation of SBF with different $HCO_3$ content and its influence on the composition of biomimetic apatites," *Acta Biomaterialia*, 2006, 2:181-189.

Munoz et al., "Interactive Effects of Albumin and Phosphate Ions on the Corrosion of CoCrMo Implant Alloy," *Journal of the Electrochemical Society*, 2007, 154(10):562-570.

Nachtrab et al., "Quantitative Material Analysis by Dual-Energy Computed Tomography for Industrial NDT Applications," *Fraunhofer EZRT*, date unknown, 1 page.

Nair and Laurencin, "Biodegradable polymers as biomaterials," *Prog. Polym. Sci.*, 2007, 32: 762-798.

Nguyen et al., "Mechanism for protection of iron corrosion by an intrinsically electronic conducting polymer," *Journal of Electroanalytical Chemistry*, 2004, 572: 225-234.

Ni et al., "Cellular localization of antiviral polyoxometalates in J774 macrophages," *Antiviral Research*, 1995, 32: 141-148.

Niinisto, "Atomic Layer deposition: A key technology for the controlled growth of oxide thin films for advanced applications," *Proc. Estonian Acad. Sci. Phys. Math.*, 2003, 52(3):266-276.

Ogata et al., "A novel anti-tumor agent, polyoxomolybdate induces apoptotic cell death in AsPC-1 human pancreatic cancer cells," *Biomedicine & Pharmacotherapy*, 2005, 59: 240-244.

Onuma et al., "Everolimus-eluting bioabsorbable stent," *Euro PCR09*, May 22, 2009, pp. 1-28.

Ormiston et al., "Bioabsorbable Coronary Stents," *Circulation Cardiovasc Intervent*, vol. 2, 2009, pp. 255-260.

Ouerd et al., "Reactivity of Titanium in Physiolgoical Medium—I. Electrochemical Characterization of the Metal/Protein Interface," *Journal of the Electrochemical Society*, vol. 154, No. 10, 2007, pp. 593-601.

Oyane et al., "Preparation and assessment of revised simulated body fluids," *Wiley Periodicals, Inc.*, 2003, pp. 188-195.

Paliwoda-Porebska et al., "On the development of polypyrrole coatings with self-healing properties for iron corrosion protection," *Corrosion Science*, 2005, 47: 3216-3233.

Peeters et al., "Preliminary Results after Application of Absorbable Metal Stents in Patients with Critical Limb Ischemia," *J. Endovasc Ther*, 2005, 12:1-5.

Peeters, et al., "Preliminary Data on Absorbable Metal Stents," *MEET 2006*, Jun. 2006, pp. 1-30.

Peuster et al., "Are resorbable implants about to become a reality," *Cardiol Young*, 2006, 16:107-116.

Pinto Slattow et al., "Optical coherence tomography and intravascular ultrasound imaging of bioabsorbable magnesium stent degradation in porcine coronary arteries," *Cardiovascular Revascularization Medicine* 9, (2008) pp. 248-254.

Purushothaman et al. "Reducing Mass-Transport Limitations by Application of Special Pulsed Current Modes". *Journal of the Electrochemical Society*. 152 (4), 2005, J33-J39.

Qasem et al., "Kinetics of paclitaxel 2'-N-methylpyridinium mesylate decomposition," *AAPS PharmSciTech*, 2003, 4(2), Article 21, 8 pages.

Quinard et al., "Development of metal/polymer mixtures for micro powder injection moulding," *10th ESAFORM Conference on Material Forming*, 2007, pp. 933-939.

Qureshi et al., "The emerging role of iron, zinc, copper, magnesium and selenium and oxidative stress in health and diseases," *Biogenic Amines*, vol. 19, No. 2, 2005, pp. 147-169.

Raman et al., "Laser assisted modification of surface microstructure for localised corrosion resistance of magnesium alloys," *Surface Engineering*, 2007, 23(2): 107-111.

Reece et al., "Metal transport studies on inherently conducting polymer membrances containing cyclodextrin dopants," *Journal of Membrane Science*, 2005, 249: 9-20.

Ren et al., "Variations of dose and electrode spacing for rat breast cancer electrochemical treatment," *Bioelectromagnetics*, 2001, 22(3):205-211.

Rettig et al., "Composition of corrosion layers on a magnesium rare-earth alloy in simulated body fluids," *Journal of Biomedical Materials Research Part A*, Oct. 18, 2006, pp. 359-369.

Rettig et al., "Corrosion resistance studies on grain-boundary etched drug-eluting stents," *J. Mater Sci: Mater Med.*, 2007, vol. 18, pp. 1377-1387.

Rettig et al., "Time-dependent electrochemical characterization of the corrosion of a magnesium rare-earth alloy in simulated body fluids," *Journal of Biomedical Materials Research Part A*, 2007, 167-175.

Rinkevich et al., "Regeneration of Amputated Avian Bone by a Coral Skeletal Implant," *Biol. Bull.*, vol. 197, Aug. 1999, pp. 11-13.

Rivers et al., "Synthesis of a novel, biodegradable electrically conducting polymer for biomedical applications," *Advanced Functional Materials*, 2002, 12: 33-37.

Russell-Stevens et al., "The effect of thermal cycling on the properties of a carbon fibre reinforced magnesium composite," *Materials Science and Engineering A*, 2005, 397: 249-256.

Schauer et al., "Protection of iron against corrosion with polyaniline primers," *Progress in Organic Coatings*, 1998, 33: 20-27.

Schinhammer et al., "Design strategy for biodegradable Fe-based alloys for medical applications," *Acta Biomaterialia*, 2009, pp. 1-9.

Schmidt et al., "Physiochemical changes in London clay adjacent to cast iron pipes," *IAEG 2006, The Geological Society of London*, Paper 313, 12 pages.

Schneider et al., "From functional core/shell nanoparticles prepared via layer-by-layer deposition to empty nanospheres," *Nano Letters*, 2004, 4: 1833-1839.

Schranz et al., "Bioabsorbable Metal Stents for Percutaneous Treatment of Critical Recoarctation of the Aorta in a Newborn," *Catheterization and Cardiovascular Interventions*, vol. 67, 2006, pp. 671-673.

Secheresse et al., "$(Mo_2O_2X_2)^{2+}$ (X=O,S), a magic building block for the design of wheel shaped metalates," *C.R. Chimie*, 2005, 8: 1927-1938.

Serruys et al., "A bioabsorbable everolimus-eluting coronary stent system (ABSORB): 2-year outcomes and results from multiple imaging methods," *The Lancet*, 2009, 373: 897-910.

Serruys, "Fourth Annual American College of Cardiology International Lecture," *Journal of the American College of Cardiology*, 2006, vol. 47, No. 9, pp. 1754-1768.

Serruys, "Glimpse into the future: bioabsorbable stents-aiming to restore vascular integrity—Introduction & Objectives," *Euro PCR09*, May 18, 2009, pp. 1-4.

Shevchenk et al., "Porous Surface of NiTi Alloy Produced by Plasma Ion Implantation," *Institute of Ion Beam Physics and Materials Research*, 2005, Strasbourg, 1 page.

Shevchenko, "Structure, composition and mechanical properties of porous layers produced by argon PIII," *Forschungszentrum Dresden*, Oct. 2007, 8 pages.

Shieh et al. "Aqueous dispersions of magnetite nanoparticles with NH3 surfaces for magnetic manipulations of biomolecules and MRI contrast agents" *Biomaterials*, 2005 26: 7183-7191.

Sieber, et al., "Investigations on the passivity of iron in borate and phosphate buffers, pH 8.4," *Corrosion Science*, vol. 48, 2006, pp. 3472-3488.

Singh Raman et al., "Laser assisted modification of surface microstructure for localised corrosion resistance of magnesium alloys," *Surface Engineering*, 2007, 23(2):107-111.

Smith et al. "Patterning self-assembled monolayers" *Progress in Surface Science*. 2004. 75:1-68.

Soto et al., "Amporphous magnesium nitride films produced by reactive pulsed lasar deposition," Journal of Non-Crystalline Solids, 2004, 342: 65-69.

Stoner et al., "The mechanism of low frequency a.c. Electrochemical Disinfection," *Bioelectrochemistry and Bioenergetics*, 1982, 9:229-243.

Su et al., "Photoacoustic imaging of coronary artery stents," *Optics Express*, vol. 17, No. 22, Oct. 26, 2009, pp. 1-8.

Sun et al., "Fabrication of a multilayer film electrode containing porphyrin and its application as a potentiometric sensor of iodide ion," *Talanta*, 1998, 46: 15-21.

Truong et al., "Corrosion protection of magnesium by electroactive polypyrrole/paint coatings," *Synthetic Metals*, 2000, 110: 7-15.

Turler et al., "Experimental low-level direct current therapy in liver metastases: influence of polarity and current dose," *Bioelectromagnetics*, 2000, 21(5):395-401.

Uhlmann et al., "Schnelle 3D-Analyse von Gefugemerkmalen" *Druckguss*, Apr. 2009, pp. 1-5.

Van Alst, "Potential conflicts of interest," *Euro PCR09*, 2009, pp. 1-22.

Virtanen et al., "Electrochemical Behavior of Fe in Phosphate Solutions Studied by In Situ X-Ray Absorption Near Edge Structure," *Journal of the Electrochemical Society*, vol. 146, No. 11, 1999, pp. 4087-4094.

Virtanen et al., "Special modes of corrosion under physiological and simulated physiological conditions," *Acta Biomaterialia*, vol. 4, 2008, pp. 468-476.

Virtanen, "Corrosion of Biomedical Implant Materials," *Corrosion of Biomedical Implant Materials*, vol. 26, Nos. 2-3, 2008, pp. 147-171.

Viswanathamurthi et al., "Preparation and morphology of niobuim oxide fibres by electrospinning," *Chemical Physics Letters*, 2003, 374: 79-84.

Volkova, "Effect of Deformation and Heat Treatment on the Structure and Properties of Magnesium Alloys of the Mg-Zn-Zr System," *Metal Science and Heat Treatment*, vol. 48, Nos. 11-12, 2006, pp. 508-512.

Volynova et al., "Mechanical Properties and the Fine Structure of Powdered Iron-Manganese Alloys," *Plenum Publishing Corp.*, 1987, pp. 999-1006.

Waksman et al., "Early-and Long-Term Intravascular Ultrasound and Angiographic Findings After Bioabsorbable Magnesium Stent Implantation in Human Coronary Arteries," *JACC: Cardiovascular Interventions*, vol. 2, No. 4, 2009, pp. 1-9.

Waksman et al., "Safety and Efficacy of Bioabsorbable Magnesium Alloy Stents in Procine Coronary Arteries," *Catherterization and Cardiovascular Intervnetions*, 2006, vol. 68, pp. 607-617.

Waksman et al., "Short-term Effects of Biocorrodible Iron Stents in Porcine Coronary Arteries," *Journal of Interventional Cardiology*, vol. 21, No. 1, 2008, pp. 15-20.

Waksman, "Update on Bioabsorbable Stents: From Bench to Clinical," *Journal of Interventional Cardiology*, vol. 19, No. 5, 2006, pp. 414-421.

Waksman, Ron, "Current state of the metallic bioabsorbable stent," Glimpse to the Future, *Euro PCR09*, 2009, pp. 1-24.

Waksman, Ron, "Why Bioabsorbale Stent Technology," Glimpse to the Future, *Euro PCR09*, 2009, pp. 1-16.

Wan et al., "Preparation and characterization of porous conducting poly(DL-lactide) composite membrances," *Journal of Membrane Science*, 2005, 246: 193-201.

Wang et al., "Polyaniline microrods synthesized by a polyoxometalates/poly(vinyl alcohol) microfibers template," *Materials Letters*, 2005, 59: 3982-3985.

Weiss et al., "Pyrrole derivatives for electrochemical coating of metallic medical devices," J. Polymer Science, Part A: Polymer Chemistry, 2004, 42: 1658-1667.

White and Slade, "Polymer electrodes doped with heteropolymetallates and their use within solid-state supercapacitors," *Synthetic Metals*, 2003, 139: 123-131.

Wilcox, "Biodegradable Technology: Medtronic Biodegradable Stent Program," *Euro PCR09*, 2009, pp. 1-25.

Windecker et al., "Biolimus-eluting stent with biodegradable polymer versus sirolimus-eluting stent with durable polymer for coronary revascularisations (LEADRERS): a randomized non-inferiority trial," *The Lancet*, Sep. 1, 2008, pp. 1-11.

Witte et al., "Biodegradable magnesium-hydroxyapatite metal matrix composites," *Biomaterials*, vol. 28, 2007, pp. 2163-2174.

Witte et al., "In Vivo Corrosion of Four Magnesium Alloys and the Associated Bone Response," *Biomaterials*, vol. 26, 2005, pp. 3557-3563.

Witte, "The history of biodegradable magnesium implants: A review," *Acta Biomaterialia*, 2010, 6: 1680-1692.

Witte, "Magnesium Corrosion: a New Challaenge for temporary Biomaterials," *Laboratory for Biomechanic and Biomaterials*, 2009, pp. 1-20.

Wuisman and Smit, "Bioresorbable polymers: heading for a new generation of spinal cages," *Eur. Spine J.*, 2006, 15: 133-148.

Xin et al., "Electrochemical Treatment of Lung Cancer," *Bioelectromagnetics*, 1997, 18:8-13.

Xu et al., "In Vivo corrosion behaviouc of Mg-MnZn alloy for bone implant application," *Journal of Biomedical Materials Research Part A*, Jun. 4, 2007, pp. 703-711.

Ye et al., "In situ synthesis of AlN particles in Mg-Al alloy by $Mg_3$-$N_2$ addition," *Materials Letters*, 2004, 58: 2361-2361.

Yen et al., "Electrochemical treatment of human KB cells in vitro," *Bioelectromagnetics*, 1999, 20:34-41.

Yfantis et al., "Novel corrosion-resistant films for Mg alloys," *Surface and Coatings Technology*, 2002, 151-152: 400-404.

Yuen et al., "Findings from an Accelerated in Vivo Corrosion Model of Magnesium," *Department of Orthopaedics and Traumatology*, date unknown, pp. 1-2.

Yun et al., "Revolutionizing Biodegradable Materials," *Materials Today*, Oct. 2009, vol. 12, No. 10, pp. 1-11.

Zarras et al., "Progress in using conductive polymers as corrosion-inhibiting coatings," *Radiation Physics and Chemistry*, 2003, 68: 3870-394.

Zberg et al., "MgZnCa glasses without clinically observable hydrogen evolution for biodegradable implants," *Nature materials*, Sep. 27, 2009, vol. 8, pp. 887-891.

Zheng, "Symposium on Biodegradable/Biocorroded metallic materials," Nov. 24, 2009, pp. 1-74.

Zhu et al., "Biocompatibility of Fe-O films synthesized by plasma immersion ion implantation and deposition," *Surface and Coatings Technology*, vol. 203, 2009, pp. 1523-1529.

Zhu et al., "Biocompatibility of pure iron: In Vitro assessment of degradation kinetics and cytotoxicity on endothelial cells," *Materials Science and Engineering*, vol. 29, 2009, pp. 1589-1582.

Zou et al., "Preparation of a phosophopolyoxomolybdate $P_2Mo_{18}O^{6-}_{62}$ doped polypyrrole modified electrode and its catalytic properties," *Journal of Electroanalytical Chemistry*, 2004, 566: 63-71.

Zucchi et al., "Electrochemical behaviour of a magnesium alloy containing rare earth elements," *Journal of Applied Electrochemistry*, 2006, vol. 36, pp. 195-204.

Macias et al., "Electrospun mesoporous metal oxide fibers," *Microporous and Mesoporous Materials*, 2005, 86: 1-13.

Authorized Officer Henrique Amaro, International Preliminary Report on Patentability from PCT/US09/043326 mailed Nov. 18, 2010, 7 pages.

Authorized Officer Jasmine Messemanne, International Search Report from PCT/US09/051965 mailed Aug. 20, 2010, 13 pages.

Authorized Officer Jasmine Messemanne, International Preliminary Report on Patentability from PCT/US09/051965 mailed Feb. 10, 2011, 8 pages.

Authorized Officer Antonio Espuch, International Preliminary Report on Patentability in PCT/US09/49422 mailed Jan. 13, 2011, 7 pages.

Authorized Officer Aurore Schneider, International Preliminary Report on Patentability from PCT/US2010/042772 mailed Feb. 4, 2011, 9 pages.

Authorized Officer Henrique Amaro, International Preliminary Report on Patentability in PCT/US2009/43326 mailed Nov. 18, 2010, 7 pages.

Authorized Officer Antoine Laurent, International Preliminary Report on Patentability in PCT/US09/046750 mailed Dec. 23, 2010, 8 pages.

Authorized Officer Mary Celine, International Search Report from PCT/US2010/060412 mailed Feb. 21, 2011, 10 pages.

Dumas et al., "Characterization of magnesium fluoride thin films produced by argon ion beam-assisted deposition," *Thin Solid Films*, 2001, pp. 61-68.

Authorized Officer Razik Menidjel, International Preliminary Report on Patentability from PCT/US09/059424, mailed May 5, 2011, 8 pages.

Peuster et al., "A novel approach to temporary stenting: degradable cardiovascular stents produced from corrodible metal-results 6-18 months after implantation into New Zealand white rabbits," *Heart*, 2001, 86(5):563-569.

\* cited by examiner

_US 8,052,745 B2_

ENDOPROSTHESIS

TECHNICAL FIELD

This invention relates to endoprostheses.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, e.g., so that it can contact the walls of the lumen. Stent delivery is further discussed in Heath, U.S. Pat. No. 6,290,721, the entire contents of which is hereby incorporated by reference herein.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn from the lumen.

SUMMARY

In an aspect the invention features a stent including a stent body and a wire-form carrying a drag passing through and located along the stent body.

In an aspect, the invention features a stent including a stent body formed of metal and a wire-form formed of metal, the wire-form carrying a drug and located along the stent body.

Embodiments may include one or more of the following features. The wire-form has a diameter of about 20 micron or less. The stent body includes fenestrations and the wire-form is located in the fenestrations. The wire-form passes through the fenestrations. The wire-form passes through a passage in the stent body. The wire-form is substantially freely slideable through the passage. The wire-form is a ceramic, metal or polymer. The drug is coated on the wire-form. The drug is in a polymer carrier. The drug is in a capsule. The wire-form is composed of multiple wire-forms joined together. The drug is provided between individual wire-forms.

Embodiments may include one or more of the following features. The wire-form extends beyond an end of the stent. The stent includes multiple wire-form strands. The density of the strands varies along the stent body. The stent body is substantially free of drug. The stent body includes an endothelialization-enhancing material on its surface. The endothelialization-enhancing material is a ceramic. The wire-form is bioerodible. The wire-form is biostable. The stent body and wire-form are formed of the same material, e.g., the same metal.

Embodiments may include one or more of the following advantages. A stent may be provided that has enhanced therapeutic, particularly drug delivery, capabilities. The drug may be carried by a thin, wire like element instead of or in addition to being on the stent body. The drug is carried by the stent but decoupled from the stent body surface. As a result, the distribution of drug delivery is not limited to the stent geometry or position of the stent wall against the vessel. Neither the stent body nor drug coating design need to be compromised to, e.g., enhance adhesion of the coating to the stent to prevent delamination. The surface of the stent wall can be optimized to enhance endothelialization. For example, the stent wall may include a ceramic coating that encourages endothelialization. In addition, more effective drug distribution beyond the vessel wall, e.g., within the fenestrated areas of the stent and/or beyond the proximal and distal ends of the stent body may be achieved.

Still further aspects, features, and advantages follow.

DESCRIPTION OF DRAWINGS

FIG. 5A is a schematic of a stent during processing, while

Like reference symbols in the various drawings indicate like elements.

DETAILED DESCRIPTION

Figure 1A:
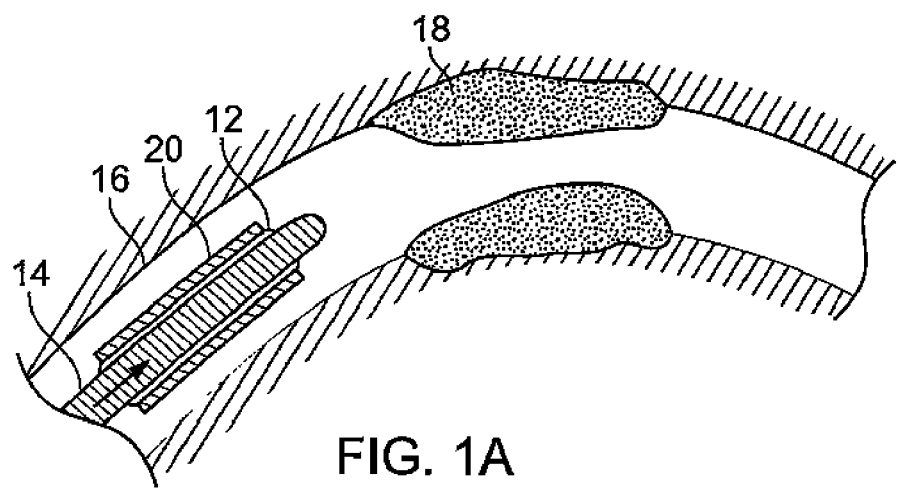
FIGS. 1A-1C are longitudinal cross-sectional views illustrating delivery of a stent in a collapsed state, expansion of the stent, and deployment of the stent.
Figure 1B:
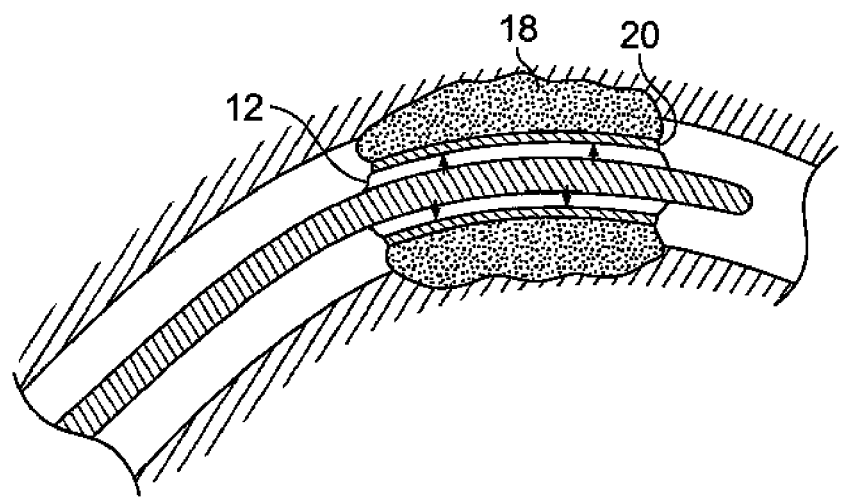
Figure 1C:
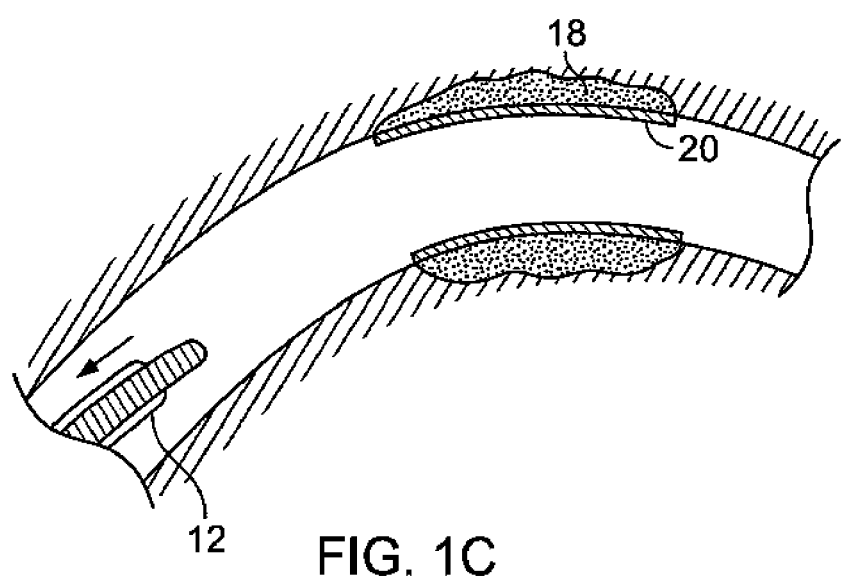

Referring to FIG. 1A, a stent 20 is placed over a balloon 12 carried near a distal end of a catheter 14, and is directed through the lumen 16 (FIG. 1A) until the portion carrying the balloon and stent reaches the region of an occlusion 18. The stent 20 is then radially expanded by inflating the balloon 12 and compressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C).

Figure 2A:
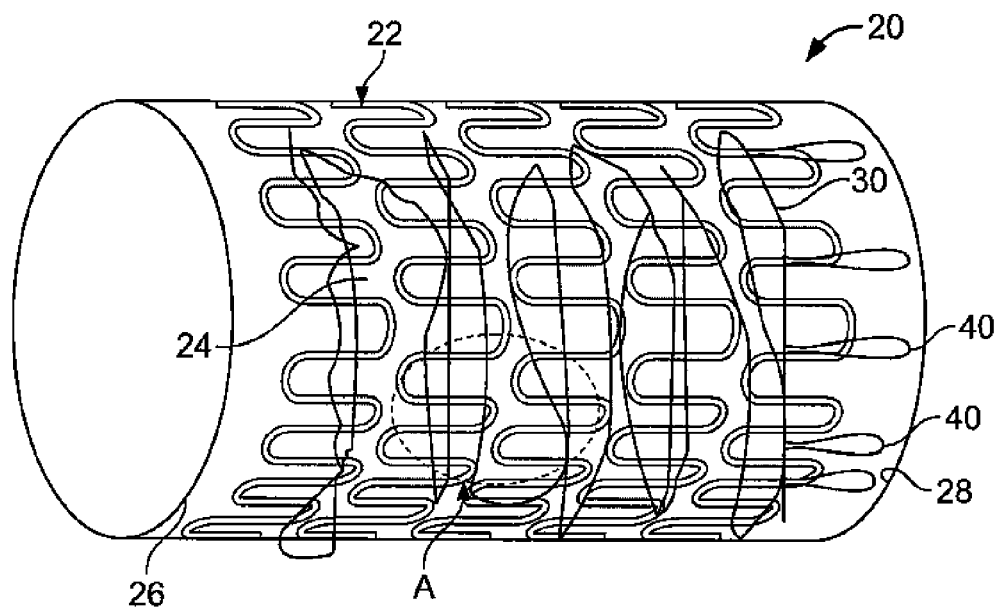
FIG. 2A is a side view of a stent.

Referring to FIG. 2A, the stent 20 includes a stent body 22 shaped to define open areas or fenestrations 24. The stent body 22 extends from a proximal end 26 to a distal end 28. The stent body 22 can be formed e.g. of a metal, ceramic, or polymer. In particular embodiments, the metal is biostable, e.g. a stainless steel, niobium, tantalum or a superelastic metal e.g. a nitinol or biodegradable, e.g. magnesium, iron or tungsten. Further discussion of stents and stent delivery is provided in Heath, incorporated supra.

Figure 2B:
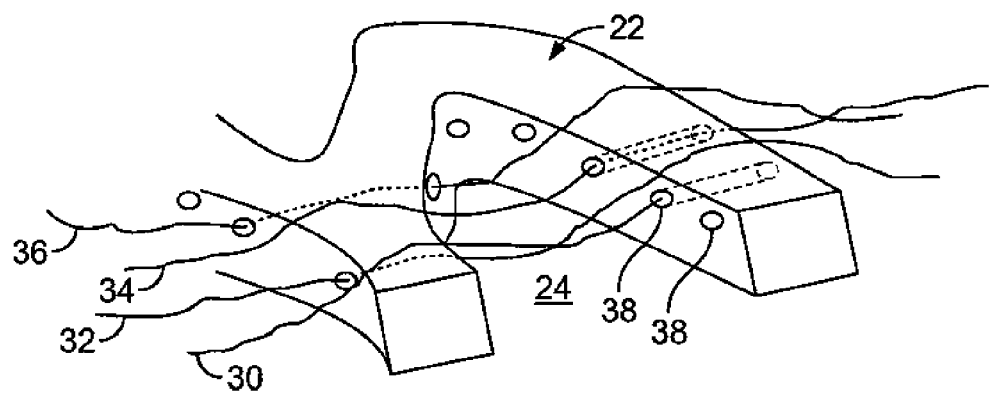
FIG. 2B is an enlarged perspective cross-sectional view of region A in FIG. 2A.

Referring as well to FIG. 2B, in embodiments, the stent body 22 is free of a drug coating and the stent includes a series of wire strands 30, 32, 34, 36 which carry a drug. The wires are elongate filament-forms that can extend over the stent body and can be woven through the fenestrations and/or through passageways 38 in the stent body. The wires can be formed of a metal, ceramic or a polymer. The drug can be contained within the wires or coated on the outside of the wires, e.g. in a drug eluting polymer coating. In embodiments, the drug eluting wire can include regions 40, in this embodiment loops, extending beyond the proximal and distal ends of the stent body.

The wires can be substantially smaller in cross-sectional dimensions than the stent body such that they do not substantially interfere with the mechanical performance of the stent body. The wires can be positioned along the stent to provide a desirable number or density at wires of desired locations along the stent. The wires can be provided at a higher density than the stent body to create a more uniform drug release profile, including within the fenestrated areas. The release profile can be selected independently of the stent body pattern. The wires can be woven to provide sufficient slack such that the wires do not inhibit expansion of the stent. The wires can extend beyond the ends of the stent, e.g. by forming loops, such that drug can be delivered beyond the ends of the stent body. A single continuous wire can be woven about the stent or multiple separate wires can be provided.

Figure 3A:
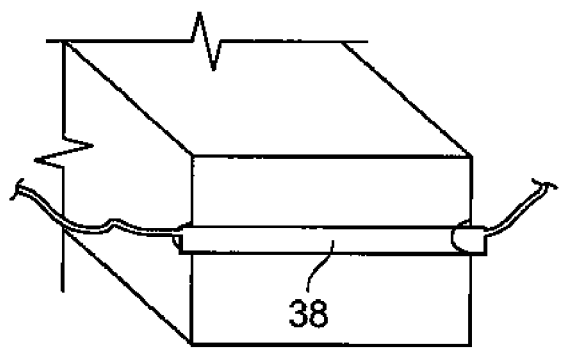
FIGS. 3A-3C are enlarged cross sections of a stent strut.
Figure 3B:
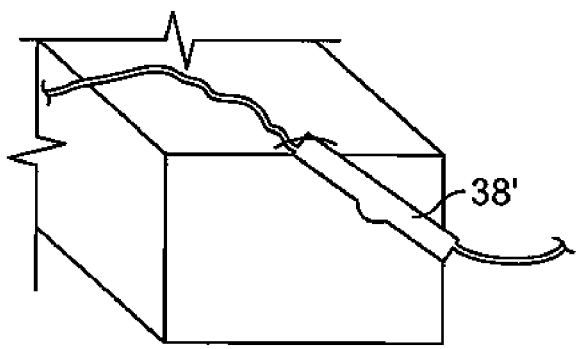
Figure 3C:
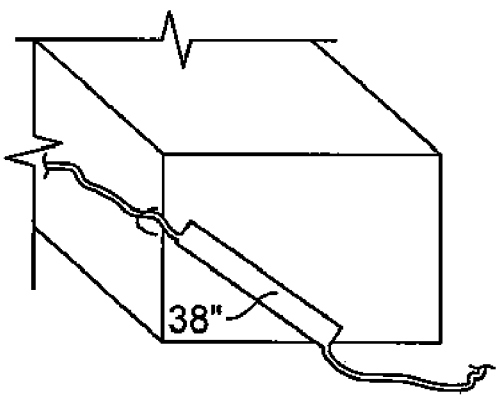

Referring to FIGS. 3A-3C, passageways 38, 38', 38" in the stent body can be, respectively, from one side surface to the other, from the outside surface to a side surface, from a side surface to an inside surface or from an outside surface to an inside surface (not shown). The passageways can be formed by laser drilling. The wires can be slideable within the passageways or can be friction fit or glued to the passageways or otherwise to the stent body. In embodiments, the wires can be tied with a knot larger than the passageway to prevent the wire from being pulled through the passageway. The wires can also be looped through the fenestrations and around the stent body and tied to hold the wires to the stent. A network of thin wires along the side-wall of stents can be formed by using two thin stents and crimping one inside of the other placing the wire network in between (like a sandwich). The two stent parts can be either glued, fused, and/or a self-expanding inner stent can be provided inside of a metal balloon expandable stent on a balloon.

In embodiments, the wires have a diameter substantially less than the thickness of the stent wall, e.g. about 20% or less, e.g. 10% or less, e.g. about 0.1 to 5%. In embodiments, the diameter is about 20 micron or less, e.g. 15 micron or less, e.g. 1-10 micron. The wires can be relatively floppy or stiff. For wires that extend beyond the ends of the stent, it is desirable the wires stay close to the vessel wall either by this areas with a higher inflammation. Further discussion of Selectins is in Eniola et al., Biomaterials 26:661-670 (2005).

Figure 4:
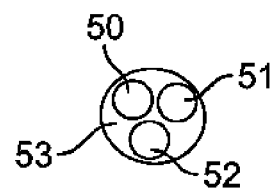
FIG. 4 is a cross section of a wire-form.

The drug is incorporated within and/or deposited on top of the wires. This can be done prior to weaving the wires through the passageways and struts, or one could attach the drug post weaving. For example, the wire can be drawn through a solution containing the drug or the drug with a matrix polymer. Damage to the coating while weaving the wire through the structure can be achieved by freezing the polymer to below its glass-transition temperature. The drug can be applied to the wire after the wire has been weaved through the stent structure, by dispensing small droplets directly to the wire. In case of a polymeric or ceramic wire, drug can be applied using electrostatic spraying. A positively charged mandrel is provided inside of the stent (not in direct contact with the stent), charges the stents negative and uses a negatively charged spray. As the spray is attracted by the core wire, it will be deflected by the stent struts, flying through the openings to the core wires, however meanwhile hitting the non-charged woven wire. The holes within the strut can be made by means of an excimer or a UV laser and ultrashort pulse (pico, femto, atto) lasers. The wire can be manipulated by hand or by automated techniques. Suitable techniques are described by, for example, the CSEM (Centre Suisse d'Electronique et de Microtechnique). Referring to FIG. 4, a string of three or more ultrafine wires 50, 51, 52 can be woven, twisted or braided, and the drug/polymer coating 53 positioned over and with the inner spaces of the braided structure between the individual wires.

Figure 5A:
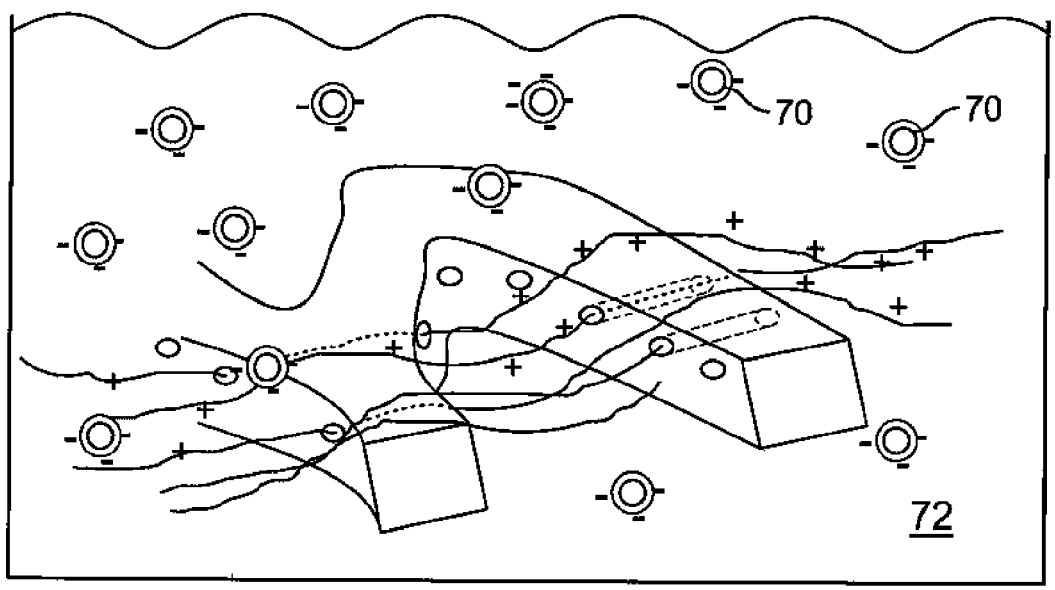
Figure 5B:
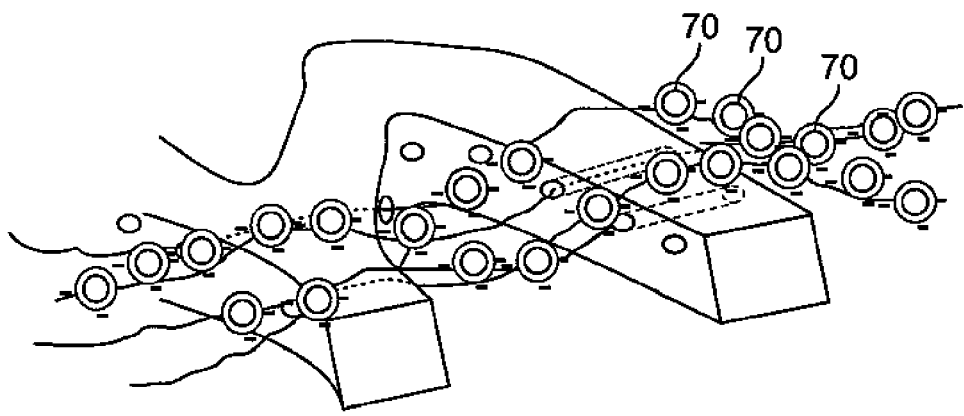
FIG. 5B is a schematic of the stent post-processing.

Referring to FIGS. 5A and 5B, the drug can be incorporated within drug release controlling and fully biodegradable capsules 70. These capsules are made using polyelectric layers and the outermost shell can therefore be made both positive as well as negatively charged. Suitable capsules are described in U.S. Published Patent Application No. 2005/0129727. Polyelectric layer techniques are described in U.S. Patent Application No. 60/845,136, filed Sep. 15, 2006. The wires can be covered with a couple of polyelectrolytic layers before weaving them through the stent structure. These layers by themselves are very thin (e.g. single nanometers) as well as robust and will survive the mechanical friction as encountered weaving the wires through the holes. After the wires have been added to the stent, the stent plus wires are dipped into a stiffness and/or the flow of body fluid through the stent. In embodiments, the wires can extend beyond the stent by about 5%, e.g. 10% or more than the length of the stent body. In embodiments, the wires extend about 0.2 to 1 cm beyond the ends of the stent. The wires can be formed of metal, ceramic, or polymer. The wires can be formed of the same material as the stent body or different material. The wires can be biostable or bioerodible. In particular embodiments, particularly with wires using biostable metals, the wires are formed of the same material as the stent body to reduce galvanic corrosion effects. In other embodiments, in which bioerosion is desireable, the stent body and wire can be formed of different metals to encourage galvanic corrosion. Suitable metals include stainless steel, niobium, titanium, magnesium, iron, and tungsten. Stainless steel wires with single micrometer diameter can be obtained from Bekaert (Belgium). Stainless steel wires are also described in Wang et al., Materials Science and Technology, 2005 Vol. 21(01) 1323. Ceramic (Alumina-oxide) fibers with diameters of 10-12 micrometer can be obtained from 3M (St. Paul, Minn.). Polymeric fibers with small dimensions can be made of dissolvable polymers using electro-spinning (see A review on polymer nanofibers by electro-spinning and their applications in nanocomposites. Composites Science and Technology 63 (2003) 2223-2253). Suitable polymers are described in US2005/0165470. The polymer may be bioerodible such that it disintegrates in a desired time in the body. In a particular embodiment wire is made out of PLGA with an embedded drug and coated as well with biotinylataead-Sialyl LewisX (sLeX), a carbohydrate that serves as a ligant to selectins, mimicking the adhesive behavior of leukocytes on selectins. The site-specific expression of selectins (P- and E-selectin) on endothelial cells of blood vessels during inflammation provides an opportunity for the targeted delivery of anti-inflammatory drugs to sites of chronic inflammation. Selectins mediate the initial interaction (rolling) of leukocytes in an inflamed vessel by binding to carbohydrate-presenting counterreceptors displayed on leukocytes. A ring or stent can be placed just proximal to a site of inflammation. Micro sized PLGA (or PLGA coated iron) wires provided on the stent or ring are coated with the (sLeX). The ends of the drug wires are allowed to extend beyond the stent or ring, flowing downstream with blood flow (anchored by the ring). Most of the wires attach themselves to the vessel wall at the location of an inflammation, providing as such a coating which self redistributes itself to solution 72 containing the drug filled capsules 70, whereby these would assemble themselves to the wires given that the charge on the wires and the charge on the capsule is opposite. As the stent surface is non-charged, no capsules will assemble on the stent surface. Optionally, different wires can be coated with different outer coating such that at a given pH, one could only coat specific wires with these capsules and other capsules with other capsules. In other embodiments, a capsule with an embedded magnetic material (e.g. Fe, magnetite) can be provided. The wires can be made magnetic (e.g. iron) to attach the capsules to the wires. The capsules can be attached after applying the wires to the stent body or even post-crimping the stent to a delivery catheter (e.g. over a balloon). Suitable capsules are discussed in Zhou et al., Nanomedicine: Nanotechnology, Biology and Medicine 1:233-237 (2005).

In embodiments, the stent body and/or the wires include endothelialization promoting material. For example, the material maybe a ceramic, such as iridium oxide with a desired morphology, such as a defined grain or striated morphology. Ceramics of desired morphology are described further in U.S. patent application Ser. Nos. 11/752,736 and 11/752,772, filed on May 23, 2007.

The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule is meant an organic molecule having 50 or fewer carbon atoms, and fewer than 100 non-hydrogen atoms in total. Exemplary therapeutic agents include, e.g., anti-thrombogenic agents (e.g., heparin); anti-proliferative/anti-mitotic agents (e.g., paclitaxel, 5-fluorouracil, cisplatin, vinblastine, vincristine, inhibitors of smooth muscle cell proliferation (e.g., monoclonal antibodies), and thymidine kinase inhibitors); antioxidants; anti-inflammatory agents (e.g., dexamethasone, prednisolone, corticosterone); anesthetic agents (e.g., lidocaine, bupivacaine and ropivacaine); anti-coagulants; antibiotics (e.g., erythromycin, triclosan, cephalosporins, and aminoglycosides); agents that stimulate endothelial cell growth and/or attachment. Therapeutic agents can be nonionic, or they can be anionic and/or cationic in nature. Therapeutic agents can be used singularly, or in combination. Preferred therapeutic agents include inhibitors of restenosis (e.g., paclitaxel), anti-proliferative agents (e.g., cisplatin), and antibiotics (e.g., erythromycin). Additional examples of therapeutic agents are described in U.S. Published Patent Application No. 2005/0216074. Polymers for drug elution coatings are also disclosed in U.S. Published Patent Application No. 2005/019265A. A functional molecule, e.g. an organic, drug, polymer, protein, DNA, and similar material can be incorporated into groves, pits, void spaces, and other features of the ceramic.

Suitable drug eluting polymers may be hydrophilic or hydrophobic. Suitable polymers include, for example, polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics such as polystyrene and copolymers thereof with other vinyl monomers such as isobutylene, isoprene and butadiene, for example, styrene-isobutylene-styrene (SIBS), styrene-isoprene-styrene (SIS) copolymers, styrene-butadiene-styrene (SBS) copolymers, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenerated polyalkylenes including polytetrafluoroethylene, natural and synthetic rubbers including polyisoprene, polybutadiene, polyisobutylene and copolymers thereof with other vinyl monomers such as styrene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collagen and derivatives thereof polysaccharides such as celluloses, starches, dextrans, alginates and derivatives of these polysaccharides, an extracellular matrix component, hyaluronic acid, or another biologic agent or a suitable mixture of any of these, for example. In one embodiment, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyiocyanates such that the devices become instantly lubricious when exposed to body fluids. In another preferred embodiment of the invention, the polymer is a copolymer of polylactic acid and polycaprolactone. Suitable polymers are discussed in U.S. Publication No. 20060038027 and U.S. Application No. 60/826,002, filed Sep. 18, 2006.

The stents described herein can be configured for vascular, e.g. coronary and peripheral vasculature or non-vascular lumens. For example, they can be configured for use in the esophagus or the prostate. Other lumens include biliary lumens, hepatic lumens, pancreatic lumens, uretheral lumens and ureteral lumens.

Any stent described herein can be dyed or rendered radiopaque by addition of, e.g., radiopaque materials such as barium sulfate, platinum or gold, or by coating with a radiopaque material. The stent can include (e.g., be manufactured from) metallic materials, such as stainless steel (e.g., 316 L, BioDur® 108 (UNS S29108), and 304 L stainless steel, and an alloy including stainless steel and 5-60% by weight of one or more radiopaque elements (e.g., Pt, Ir, Au, W) (PERSS®) as described in US-2003-0018380-A1, US-2002-0144757-A1, and US-2003-0077200-A1), Nitinol (a nickel-titanium alloy), cobalt alloys such as Elgiloy, L605 alloys, MP35N, titanium, titanium alloys (e.g., Ti-6Al-4V, Ti-50Ta, Ti-10Ir), platinum, platinum alloys, niobium, niobium alloys (e.g., Nb-1Zr) Co-28Cr-6Mo, tantalum, and tantalum alloys. Other examples of materials are described in commonly assigned U.S. application Ser. No. 10/672,891, filed Sep. 26, 2003; and U.S. application Ser. No. 11/035,316, filed Jan. 3, 2005. Other materials include elastic biocompatible metal such as a super-elastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. application Ser. No. 10/346,487, filed Jan. 17, 2003.

The stent can be of a desired shape and size (e.g., coronary stents, aortic stents, peripheral vascular stents, gastrointestinal stents, urology stents, tracheal/bronchial stents, and neurology stents). Depending on the application, the stent can have a diameter of between, e.g., about 1 mm to about 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stent can be balloon-expandable, self-expandable, or a combination of both (e.g., U.S. Pat. No. 6,290,721). The ceramics can be used with other endoprostheses or medical devices, such as catheters, guide wires, and filters.

All publications, patent applications, patents, and other references mentioned herein are incorporated by reference herein in their entirety.

Still further embodiments follow.

What is claimed is:

1. A stent comprising
    a stent body defining a lumen and a stent body surface, the stent body comprising a first metal, the stent body surface defined by a luminal surface, an abluminal surface, and at least two side surfaces of the stent body, and
    a wire-form formed of a second metal, said wire-form carrying a drug and passing through and located along the stent body without substantially interfering with mechanical performance of the stent body, the second metal being bioerodible and different from the first metal of the stent body, thereby to encourage galvanic corrosion of the wire-form,
    the drug on the wire-form being decoupled from the stent body surface, and
    delivery of the drug not being limited by geometry of the stent body or by position of the stent body surface against a vessel wall,
    wherein the stent body includes passageways formed therethrough, at least one passageway having an opening in at least one side surface of the stent body and extending along the longitudinal axis of the stent body, and
    wherein the wire-form passes through the passageways.

2. The stent of claim 1, wherein the wire-form has a diameter of about 20 microns or less.

3. The stent of claim 1, wherein the wire-form is substantially freely slideable through the passageways.

4. The stent of claim 1, wherein the drug is coated on the wire-form.

5. The stent of claim 4, wherein the drug is in a polymer carrier.

6. The stent of claim 5, wherein the drug is in a capsule.

7. The stent of claim 1 wherein the wire-form comprises multiple wire-forms joined together.

8. The stent of claim 7 wherein the drug is provided between individual wire-forms of the multiple wire-forms.

9. The stent of claim 1 wherein the wire-form extends beyond an end of the stent.

10. The stent of claim 1 wherein the stent includes multiple wire-form strands.

11. The stent of claim 10 wherein the density of the strands varies along the stent body.

12. The stent of claim 1 wherein the stent body is substantially free of drug.

13. The stent of claim 1 wherein the stent body includes an endothelialization-enhancing material on the stent body surface.

14. The stent of claim 13 wherein the endothelialization-enhancing material is a ceramic.

15. The stent of claim 1 wherein the drug comprises a drug release profile independent of a pattern of the stent body.

16. The stent of claim 1 further comprising an additional, coaxial stent body, the wire-form being disposed between the stent body and the additional stent body.

17. The stent of claim 1 wherein the wire-form has a diameter substantially less than a thickness of the stent body.

18. The stent of claim 17 wherein the stent body comprises a continuous tubular element formed of a metal, a polymer, or a ceramic.

19. The stent of claim 1, wherein the wire-form is magnetic.

20. The stent of claim 1, wherein the passageways are formed by an excimer laser, a UV laser, or ultrashort pulse lasers.

* * * * *

UNITED STATES PATENT AND TRADEMARK OFFICE
CERTIFICATE OF CORRECTION

| | | |
|---|---|---|
| PATENT NO. | : 8,052,745 B2 | Page 1 of 1 |
| APPLICATION NO. | : 11/854966 | |
| DATED | : November 8, 2011 | |
| INVENTOR(S) | : Jan Weber | |

It is certified that error appears in the above-identified patent and that said Letters Patent is hereby corrected as shown below:

1.) Title Page; Section (57) Abstract; Line 1: after "embodiments" insert --,--.

Signed and Sealed this
Twentieth Day of March, 2012

David J. Kappos
*Director of the United States Patent and Trademark Office*